United States Patent
Wong et al.

(10) Patent No.: US 7,766,846 B2
(45) Date of Patent: Aug. 3, 2010

(54) RAPID BLOOD EXPRESSION AND SAMPLING

(75) Inventors: Daniel Wong, Sunnyvale, CA (US); Paul Patel, Sunnyvale, CA (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 12/020,766

(22) Filed: Jan. 28, 2008

(65) Prior Publication Data
US 2009/0192409 A1 Jul. 30, 2009

(51) Int. Cl.
A61B 5/00 (2006.01)
A61B 17/14 (2006.01)
A61B 17/32 (2006.01)
B65D 81/00 (2006.01)

(52) U.S. Cl. ............ 600/583; 600/573; 600/584; 606/181; 606/182

(58) Field of Classification Search ........... 600/573, 600/576, 583, 584
See application file for complete search history.

(56) References Cited

U.S. PATENT DOCUMENTS

| | | | |
|---|---|---|---|
| 2,706,482 A | 4/1955 | Griffitts | |
| 2,801,633 A | 8/1957 | Ehrlich | |
| 4,218,421 A | 8/1980 | Mack, Jr. et al. | |
| 4,577,630 A | 3/1986 | Nitzsche et al. | |
| 4,712,548 A | 12/1987 | Enstrom | |
| 5,423,847 A | 6/1995 | Strong et al. | |
| 5,582,184 A | 12/1996 | Erickson et al. | |
| 5,591,139 A | 1/1997 | Lin et al. | |
| 5,709,699 A | 1/1998 | Warner | |
| 5,797,940 A | 8/1998 | Mawhirt et al. | |
| 5,801,057 A | 9/1998 | Smart et al. | |
| RE36,268 E | 8/1999 | Szuminsky et al. | |
| 6,063,040 A | 5/2000 | Owen et al. | |
| 6,230,051 B1 | 5/2001 | Cormier et al. | |
| 6,306,104 B1 | 10/2001 | Cunningham et al. | |

(Continued)

FOREIGN PATENT DOCUMENTS

EP 0 199 484 B1 10/1986

(Continued)

OTHER PUBLICATIONS

U.S. Appl. No. 11/466,202, filed Aug. 22, 2006 to Patel et al.

(Continued)

*Primary Examiner*—Max Hindenburg
*Assistant Examiner*—Adam J Eiseman
(74) *Attorney, Agent, or Firm*—Woodard, Emhardt, Moriarty, McNett & Henry LLP

(57) ABSTRACT

Body fluid sampling device comprising a skin-piercing element having a collection zone for receiving body fluid, the device further comprising a fluid receiving means remotely spaced apart from the collection zone so that body fluid in the collection zone will not contact the fluid receiving means initially. The collection zone takes up a very small volume of body fluid of about 10 to 500 nl in a very short time period of less than 0.5 seconds. The fluid receiving means may have a test zone for performing an analytical reaction. Fluid sample from the collection zone is automatically or manually transported to the fluid receiving means to contact the fluid with the test zone.

47 Claims, 23 Drawing Sheets

U.S. PATENT DOCUMENTS

| | | |
|---|---|---|
| 6,319,210 B1 | 11/2001 | Douglas et al. |
| 6,332,871 B1 | 12/2001 | Douglas et al. |
| 6,364,889 B1 | 4/2002 | Kheiri et al. |
| 6,589,260 B1 * | 7/2003 | Schmelzeisen-Redeker et al. ............ 606/181 |
| 6,612,111 B1 | 9/2003 | Hodges et al. |
| 6,939,312 B2 | 9/2005 | Hodges et al. |
| 7,025,774 B2 | 4/2006 | Freeman et al. |
| 7,276,146 B2 | 10/2007 | Wilsey |
| 2002/0137998 A1 | 9/2002 | Smart et al. |
| 2002/0168290 A1 * | 11/2002 | Yuzhakov et al. ............ 422/56 |
| 2003/0018282 A1 | 1/2003 | Effenhauser et al. |
| 2003/0028125 A1 | 2/2003 | Yuzhakov et al. |
| 2003/0050573 A1 | 3/2003 | Kuhr et al. |
| 2003/0073931 A1 | 4/2003 | Boecker et al. |
| 2003/0212344 A1 | 11/2003 | Yuzhakov et al. |
| 2004/0031682 A1 | 2/2004 | Wilsey |
| 2005/0171567 A1 | 8/2005 | DeHart |
| 2005/0215923 A1 | 9/2005 | Weigel |
| 2006/0020228 A1 | 1/2006 | Fowler et al. |
| 2006/0155317 A1 | 7/2006 | List |
| 2006/0173379 A1 | 8/2006 | Rasch-Menges et al. |
| 2006/0247555 A1 | 11/2006 | Harttig |
| 2006/0293611 A1 * | 12/2006 | Calasso et al. ............ 600/583 |
| 2007/0016103 A1 | 1/2007 | Calasso et al. |
| 2007/0197937 A1 * | 8/2007 | Sarofim et al. ............ 600/583 |
| 2007/0276290 A1 * | 11/2007 | Boecker et al. ............ 600/583 |
| 2009/0054811 A1 * | 2/2009 | Boecker ............ 600/583 |

FOREIGN PATENT DOCUMENTS

| | | |
|---|---|---|
| EP | 0 299 517 B1 | 6/1993 |
| EP | 0 565 970 B1 | 6/1994 |
| EP | 0 723 418 B1 | 7/1996 |
| EP | 1 101 443 A2 | 5/2001 |
| EP | 1 346 686 A2 | 9/2003 |
| EP | 1 360 931 A1 | 11/2003 |
| EP | 1 424 040 A1 | 6/2004 |
| EP | 1 532 996 A1 | 5/2005 |
| EP | 1 787 584 A1 | 5/2005 |
| WO | WO 97/42888 A1 | 11/1997 |
| WO | WO 01/66010 A1 | 9/2001 |
| WO | WO 01/72220 A1 | 10/2001 |
| WO | WO 02/50534 A1 | 6/2002 |
| WO | WO 02/062210 A1 | 8/2002 |
| WO | WO 02/062242 A1 | 8/2002 |
| WO | WO 2004/064903 A1 | 8/2004 |
| WO | WO 2005/084530 A2 | 9/2005 |
| WO | WO 2005/084545 A1 | 9/2005 |
| WO | WO 2005/084546 A3 | 9/2005 |
| WO | WO 2006/072004 A2 | 7/2006 |

OTHER PUBLICATIONS

U.S. Appl. No. 11/549,302, filed Oct. 13, 2006 to Roe et al.
International Patent Application PCT/EP2009/000413 International Search Report and Written Opinion mailed May 4, 2009.
International Patent Application PCT/EP2009/000413 International Preliminary Report on Patentability mailed Dec. 18, 2009.

* cited by examiner

RAPID BLOOD EXPRESSION AND SAMPLING

BACKGROUND

The present application generally concerns the field of collecting and analyzing body fluid samples.

Portable blood testing equipment, such as for blood glucose, cholesterol, etc., has gained in popularity in home diagnostic, medical, and/or veterinary environments due to their improved convenience. One significant drawback in portable testing is the pain associated with lancing the skin to collect a fluid sample. Pain can be reduced by penetrating the skin at shallower depths, but less blood and/or interstitial fluid is typically produced. For the home diagnostic market, consumers want the test to be painless, convenient, and short so as to minimally interfere with day-to-day activities. In the present market place, non-integrated testing products dominate in which separate lancets and test strips are used to produce and analyze the fluid sample. However, to ensure a successful test, these non-integrated approaches usually require relatively large sample volumes, and hence, they need painfully deep incisions. Due to the number of separate steps involved, these non-integrated systems are not very convenient and require a significant amount of time to perform a successful test.

Integrated disposables have been proposed that incorporate some type of lancet or needle with a testing means like a test strip such that lancing, fluid collection, and sample analysis steps occur almost instantaneously within a single unit. While integrated disposables are more convenient and can collect smaller blood samples at shallower penetration depths, integrated disposables have yet to achieve commercial success due to a number of factors. Commercially successful integrated disposables have not been implemented due to several factors. One major factor is the low success test rate of the current batch of integrated disposables. Current testing methodologies use separate lancets and test strips. In a traditional test, the lancet is used to pierce the skin, and when a drop of blood forms on the skin, the separate test strip is used to collect and analyze the sample. With these current methodologies, if one of the steps proves problematic, other steps or options can be taken such that a useful test can be obtained without the need for abandoning the entire procedure. In other words, with the traditional non-integrated approach, users can intervene in the collection process so as to ensure that a successful test can be performed. For example, the user can re-lance the skin and/or pinch the skin around the incision to express additional fluid without wasting a test strip. In contrast, the various sources of fluid collection failures in integrated disposables are cumulative in nature such that a failed test leads to the complete loss of the integrated disposable. Typically with integrated disposables a user gets one shot so all of the various steps of piercing the skin, drawing the fluid, and analyzing the fluid must be performed flawlessly. If one step is unsuccessful, the entire test fails, and the integrated disposable is usually wasted and replaced with a new one, thereby eliminating some of the advantages of integrated systems. As should be recognized, these test failures can make the operational costs for the system quite expensive. Further, this need for multiple attempts to conduct a successful test can frustrate the user.

Thus, there is a need for improvement in this field.

SUMMARY

In view of the above-mentioned issues, the inventors discovered that the problem of collecting fluid with an integrated disposable to achieve a high collection success rate is solved by piercing the skin and collecting body fluid from the skin before reflexive action occurs. Reflexive action generally occurs in response to the pain associated with piercing the skin during sample collection. By way of example, when someone cuts their finger, their first tendency is to pull the finger away from the pain source. While this reflexive action is useful in many instances to avoid further injury, this reflexive movement can be detrimental to body fluid collection and testing. In particular, the user can jerk or move their finger or other body part away from the collection device before an adequate sample can be collected. Furthermore, the finger or other body part can become tense as a result of the pain, thereby constricting blood vessels and reducing associated bleeding. The reflexive movement can also damage the device as well as knock fluid out the device resulting in an unsuccessful test. On the other hand, by collecting the body fluid and removing the skin piercing device, such as a lancet or needle, from the skin or other tissue before the reflexive action occurs, the fluid can be collected at a high success rate.

Under current pain theory, nerve impulses for pain tend to travel at a speed of about 10 meters per second (m/s). Depending on the size, age, health, etc. of an individual, it would be expected that the reaction time for pain sensed on the finger to be around 200 to 500 milliseconds (ms). In tests conducted by the inventors, it was found that the fastest reaction time to pain was about 150 ms for a tested individual. Besides sensing pain, reflexive action can occur as a result of other sensory cues, such as visual or auditory stimuli. For example, simple reaction time to detect the onset of a light flash is approximately 200 to 300 ms. The best athletes' reaction times to auditory stimuli, such as to a starter's pistol in track, are usually in the range of about 120 to 160 ms. As a result of their insight and bolstered by test results, the inventors discovered that it is desirable to remove the piercing member from the incision within about 200 ms and more particularly within about 150 ms. To provide a safety buffer, it is therefore desirable that the whole piercing process occurs no longer than 100 ms. As will be recognized below, the inventors have collected body fluid samples at commercially successful levels by withdrawing the piercing member within about 75 ms of initial penetration of the piercing member.

Inaccurate test results can also be a concern as well as a source for failed tests in integrated devices. As mentioned before, fluid sample sizes for integrated devices can be relatively small, that is, in the sub-microliter range. In one particular example, sample volumes can range from 20 to 200 nanoliters (nl) while still achieving accurate test results in a relatively short period of time. These smaller sample sizes enable quicker tests, but they are prone to numerous sources of inaccuracies, and as a practical matter, there is a lower volume limit for accurately testing a fluid sample. The inventors found that one source for inaccurate test results in samples in the sub-microliter or nanoliter range is caused by the evaporation of liquid during fluid collection as well as analysis. In these tiny test volumes, even slight variations in volume can create significant differences in analyte concentration measurements. It was discovered that integrated devices with open capillary channels are especially susceptible to fluid evaporation problems. The problem of inaccurate test results for sample sizes less than one microliter in integrated devices with open capillary channels is solved by drawing and depositing the sample on the sample analysis means within 500 ms of piercing the skin. In other aspects, the fluid is deposited within 150 or 200 ms to further reduce evaporation, and in a further aspect, the fluid is deposited within 100 ms and even 75 ms which provides further benefit.

By depositing the collected fluid in such a rapid fashion only minimal evaporation can occur, thereby leading to more accurate results.

To achieve high fluid collection success rates for integrated devices in a short time, the inventors discovered that at least three general factors contribute to successful fluid collection: the tip design of the piercing member; the piercing profile; and the amount of force applied against the skin. Further, the inventors discovered that none of the above-mentioned factors alone lead to consistent and rapid fluid collection. Instead, a specific combination and levels of these factors were needed. In particular, the inventors discovered that the problem of collecting fluid to achieve a high collection success rate was solved by pressurizing the fluid beneath the skin so that body fluid is easily introduced into a capillary channel that has a channel entrance offset from the tip of the piercing member and withdrawing the piercing member from the skin at a slower speed than during the penetration stroke into the skin with the piercing member being completely removed from the skin before reflexive action occurs.

Considering the relatively short time frame that the piercing member has to collect fluid, the capillary channel in the piercing member at times might not sufficiently fill before being withdrawn from the skin. It is hypothesized that the viscosity or other properties of the blood (and/or other body fluid) being collected might limit the rate at which the capillary channel can be filled. The issue of collecting an adequate amount of body fluid for testing before the subject reacts to the pain associated with piercing the skin with a piercing member is solved by completely filling the capillary channel with body fluid adhered to the piercing member after withdrawal of the piercing member from the skin. In other words, the inventors discovered that it is not necessary to have all of the sample within the capillary channel before the piercing member is withdrawn, but only the sample inside the capillary channel and/or adhered to the piercing member at a position capable of being drawn into the capillary channel after withdrawal is needed. As alluded to before, it was unexpectedly found that the tip design of the piercing member played a role in successful fluid collection. In one embodiment, the tip of the piercing member has been designed such that body fluid remains adhere to the entrance of the capillary channel after the piercing member is withdrawn from both the skin and any fluid pooling on the surface of the skin.

While not previously recognized to be a factor in fluid collection speed, it was surprisingly discovered that the offset distance of the capillary channel entrance was a factor for increasing the speed of fluid collection. In one particular aspect, the entrance of the capillary channel in the piercing member is offset a specified distance from the tip of the piercing member. The inventors found that if the entrance of the capillary channel was too close, the relative pain created by piercing the skin was unacceptably high. Moreover, it was unexpectedly discovered that with the short piercing times involved, insufficient sample volumes for testing were collected when the capillary entrance was too close to the tip. While not having a definitive answer, the inventors have several theories that might explain this result. One theory is that having the capillary entrance close to the tip made only a small pooling area for fluid beneath the skin. Another potential theory is that the relative closeness of the capillary entrance to the tip prevents fluid from adhering to the piercing member after withdrawal because the fluid on the piercing member drains back or adheres to the drop of fluid on the skin and/or to the incision. It was thought that increasing the distance between the capillary channel entrance and the tip of the piercing member would improve collection success rates because the volume of the pooling would be larger. However, it was unexpectedly discovered that the capillary channel entrance can be too far from the tip of the piercing member so as to be detrimental to the success rate for fluid collection. While not knowing the actual source of this unexpected outcome, it is theorized that this might be the result of the capillary channel entrance being too far away such that less fluid from the incision is able to adhere to the capillary channel entrance before being withdrawn from the skin. In one aspect, it was discovered that positioning the opening or entrance of the capillary channel between 350 to 600 micrometer (μm) from the tip provided the desired collection success rate, and in a more specific embodiment, the entrance of the capillary channel is located between 382 to 5730 μm from the tip. In one particular embodiment, the opening is desirably located about 425 μm from the tip. As will be appreciated, the tip design of the piercing member may be beneficial for other aspects of rapid fluid collection as well.

To achieve rapid and accurate fluid collection, the inventors also found that pressure had to be applied to the skin. In particular, it was discovered that between 10 to 12 Newtons (N) of force needs to be applied to an expression ring in order to rapidly express the fluid. Any force applied to the skin greater than 12 N tends to create significant pain and/or lead to injury. Upon further experimentation, the inventors found that applying 8 N of force created commercially acceptable results and at least 6 N of force could be applied by an expression ring in some instances and quick fluid collection was still practical. In essence, pressing the expression rings against the skin at the specified force pressurized the blood beneath the skin, which in turn probably caused the pressurized blood to be injected into the capillary channel in a rapid fashion.

The piercing profile was also found as a factor for promoting rapid fluid collection. In particular, it was found that a rapid piercing (in) stroke, followed by a longer withdraw (out) stroke tended to minimize pain as well as promote fluid collection. It was found that a constant withdraw stroke or a withdraw stroke having a certain dwell time beneath the skin followed by a rapid withdraw from the skin were both suitable for rapid fluid collection purposes. In one particular aspect, a 3 to 5 ms piercing stroke followed by a longer 70 to 197 ms withdraw time achieved rapid and consistent results. During piercing, the typical penetration depth of the piercing member was set to around 1.6 mm, but the actual penetration depth could vary as much as from 0.8 to 1.2 mm.

Other aspects relate to the particular features of the expression member as well as the specific dimensions of the piercing member so as to minimize pain and enhance fluid collection. In one aspect, the tip has an included or blade angle between 20° to 40°, and more preferably of about 30°. The shank of the tip has a width between 300 to 700 μm and in one particular form has a width of about 300 μm. The piercing member has a thickness between 50 to 150 μm and in one particular form has a thickness of about 127 μm. The capillary channel in the tip is hydrophilic and has an aspect ratio (depth/width) from about 0.7 to 1.6, and in one particular form, the capillary channel has an aspect ratio of about 1.4.

Other features and benefits will be appreciated from the following detailed description.

DESCRIPTION OF SELECTED EMBODIMENTS

Figure 1:
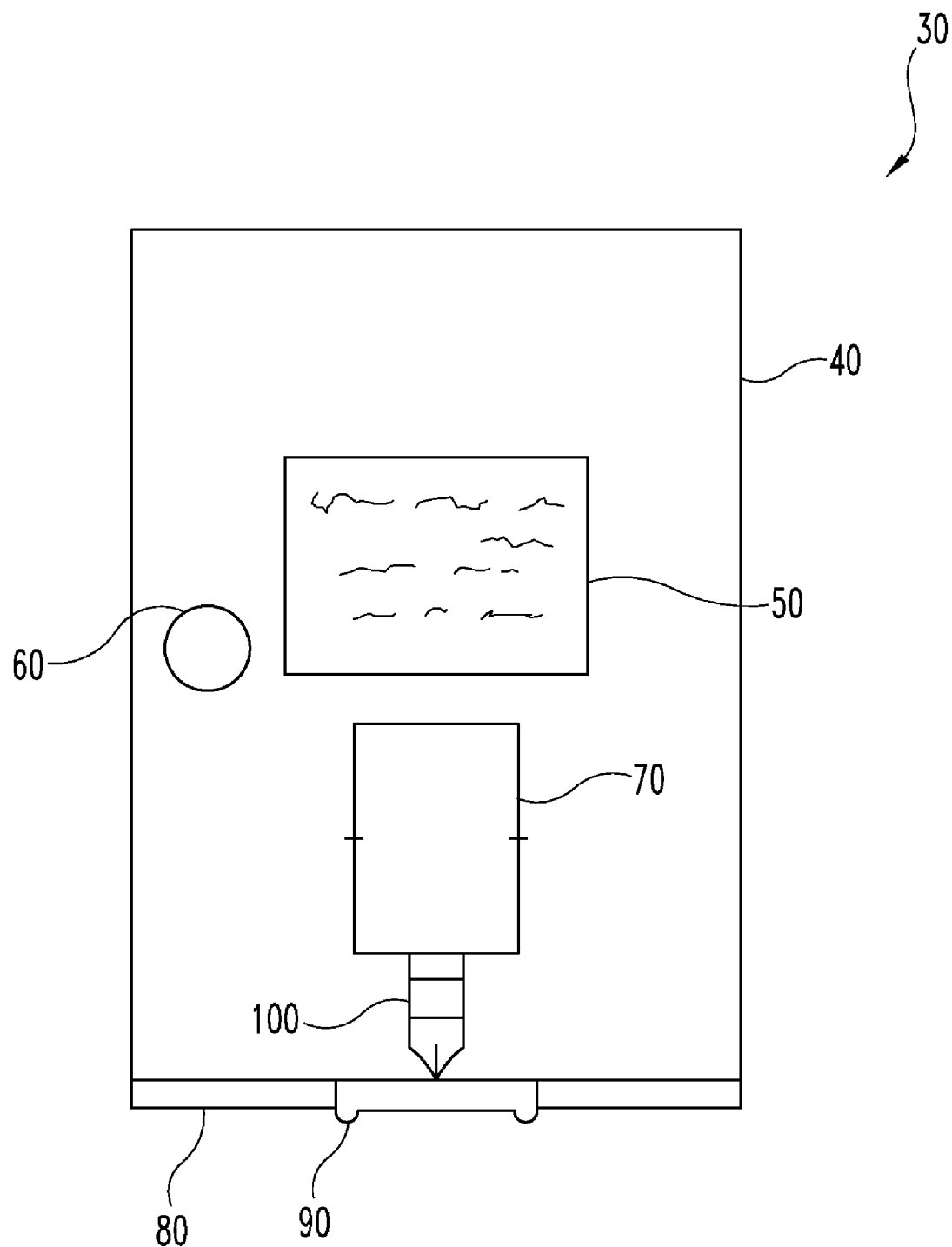
FIG. 1 is a diagrammatic view of an integrated meter system according to one embodiment.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments and any further applications of the principles of the invention as described herein are contemplated as would normally occur to one skilled in the art to which the invention relates.

As previously discussed at length, it has been a goal in the diagnostics industry to develop a commercially viable integrated testing device. The term "integrated device" has been commonly used in industry to refer to an apparatus that automatically performs all the various steps needed to test body fluids (like blood, interstitial fluid, etc.). These steps in integrated devices usually include piercing the skin or other tissue, drawing the sample of body fluid from skin, and testing the sample as well as optionally expressing or otherwise promoting production of body fluid from the incision. Although integrated devices have been commercially sold, such as the MEDISENSE® SOF-TACT™ brand diabetes management system, these integrated devices have so far commercially failed in the market place due to several factors, including the bulkiness of the device and low test success rates. As alluded to before, test reliability or success is especially important in integrated devices because, due to their automatic nature, it is very difficult to correct for testing errors midstream during a test.

Integrated disposables have been proposed in which the various components that come in contact with the body fluid are discarded and replaced with a new one after each test so as to avoid the issues of cross contamination. These integrated disposables typically can analyze and collect smaller sample sizes, thereby increasing the flexibility in where fluid can be collected from the body as well as reducing the pain associated with fluid collection. In industry, the term "integrated disposable" commonly refers to a relatively small and inexpensive devices that perform most or all of the testing steps, such as piercing the skin, drawing the sample, and at least in part analyzing the sample. Integrated disposables usually incorporate some type of piercing means, like a lancet or needle, along with a testing or analysis means, such as test strips and/or chemicals, for analyzing the sample. The testing means on the integrated disposable commonly includes electrodes, enzymes, reagents, mediators, and the like for analyzing the fluid. The meter in which the integrated disposable is loaded includes electronics, displays, etc. that along with the testing means of the integrated disposable facilitate analysis of the sample using any number of analysis techniques, such as electrochemical and/or photometric techniques to name a few examples. Normally, the meter contains the more expensive components, whereas the integrated disposable contains the less expensive components that can be disposed of after each use. In most instances, the testing means is in some way secured to the piercing means, but there are some integrated disposable designs in which the piercing means and testing means are only associated together for a brief period of time during testing.

Integrated disposables can be further subcategorized into specific design classes. Some more common integrated disposable types includes lancet integrated test elements (or "LITs" for short) and "micro-samplers." LITs usually are considered integrated disposables in which a test strip is secured to a lancet in either a fixed or moveable manner. LITs typically collect body fluid from the surface of the skin in a fashion analogous to a vampire bat. Micro-samplers on the other hand generally collect most of the body fluid beneath the skin in a manner similar to a mosquito. The term "micro-samplers" typically refers to an integrated disposable with a piercing member that is similar in function to a needle that is attached or otherwise associated with the testing means. The piercing member in the micro-sampler has a capillary channel that draws body fluid beneath the skin onto the testing means. The capillary channel in the micro-sampler can have a closed design, an open design, or a combination of both. In the closed capillary channel design, only the end of the capillary channel at the tip is open to the environment and thus able to collect fluid. On the other hand, in the open capillary design, the entire length of the capillary channel is open to the environment and thus able to collect fluid. The open capillary channel design can simplify manufacturing as well as improve fluid collection because fluid can be collected along its entire length and even above the surface of the skin. However, the inventors discovered a problem with these open capillary designs that in some instances can affect the test results. In particular, given micro-samplers typically collect fluid in the sub-micro liter range (less than 1 µl), in some instances from 20 to 200 nl, the inventors discovered that evaporation along the open capillary channel, even ever so slightly, can change concentration levels and hence, detrimentally affect the test results. It was found that the open capillary channel created a relatively large surface area for the sample that promoted evaporation. The inventors discovered that drawing the sample and rapidly depositing the sample onto the testing means significantly reduced the effects of evaporation. Specifically, the inventors found that depositing the sample onto the testing means within 500 ms from initial piercing of the skin reduced evaporation. There was a question as to whether such rapid depositing of fluid was even possible. Nevertheless, it was further found that depositing the fluid even within 150 or 200 ms was possible, which further reduced evaporation, and depositing within 100 ms and even 75 ms provided further benefits.

As noted before, one of the main hurdles for achieving a commercially successful integrated device is the ability to reliably collect fluid samples on a consistent basis. With traditional non-integrated approaches, users can intervene in the collection process so as to ensure that a successful test can be performed. Integrated devices, especially integrated disposables, automatically perform the fluid collection steps and hence do not generally have the luxury of repeating steps to ensure success. High fluid collection success rates are one of the main factors that determine whether an integrated device will become commercially viable. For the purposes of determining collection success rates, a test is considered successful when a body fluid sample is collected that has sufficient volume so that the testing means is able to accurately analyze the fluid sample. Volume sufficiency for the testing means is dependent on the testing technique used. Today, most current test strips, such as photometric and electrochemical test strips, are able to adequately analyze fluid samples having volumes less than 1 μl within 10 seconds or less and even within 5 seconds. However, the sample volumes can be too small to achieve accurate test results. Today's testing technologies in other words do have limits as to the minimum fluid volumes needed for accurate fluid analysis. Current commercial products are able to accurately test around 200 to 300 nl of body fluid as a minimum. It is possible that this minimum volume for accurate testing can be reduced to 20 nl with present day technology/chemistry, but right now, any sample volumes smaller than 20 nl are unlikely to produce accurate test results on a consistent basis. It has been considered that the minimum requirements for the fluid collection success rates for a commercially acceptable integrated device needs to be at least around 80%. As a practical matter, the success rates should be at or over 95% for a commercially successful integrated device. As of now, the inventors are unaware of any commercial integrated disposables or other integrated devices that are able to achieve these high fluid collection success rates in real world conditions.

One main factor the inventors discovered that is detrimental to fluid testing success in the real world is the reflexive action that occurs as a result of the pain experienced during piercing of the skin. It was found that the problem of collecting fluid with an integrated device to achieve a commercially acceptable collection success rate is solved by piercing the skin, collecting body fluid from the skin, and removing the piercing member from the skin before reflexive action occurs. In worst case scenarios, depending on the individual, the reflexive action can occur within about 200 ms from initial piercing of the skin. Therefore, the inventors found it desirable to remove the piercing member from the incision within about 200 ms and more particularly within about 150 ms of initially piercing the skin. Further successful testing was achieved within 100 ms and even 75 ms of initial penetration of the piercing member, which provides a further safety buffer.

It was originally thought that trace amounts of only a few nanoliters of fluid might be collected in a rapid fashion, but realistically, the sample volumes collected would be too small for accurate testing. As mentioned before, fluid collection is only considered successful when the volume of fluid collected is enough to perform an accurate test, which under current technology is anywhere from theoretically 20 nl under ideal conditions to 200 nl at a minimum under actual testing conditions. One of many unexpected findings was that not all of the fluid needed to be inside the capillary channel upon removal of the piercing member from the skin. Rather, the body fluid could be adhered on the piercing member outside the capillary channel upon withdrawal from the skin and later drawn into the capillary channel. Piercing members with open capillary channel designs were helpful in this regard, because fluid can be drawn in along the entire length of the capillary channel.

To achieve high fluid collection success rates for integrated devices in a short time, the inventors discovered that three general factors generally contributed to successful fluid collection: the amount of force applied against the skin; the tip design of the piercing member; and the piercing profile. Further, the inventors discovered that none of the above-mentioned factors alone lead to consistent and rapid fluid collection. Instead, a specific combination and levels of these factors were needed. Specifically, for successful fluid collection to occur on a commercially acceptable basis in a such a short period of time (i.e., before reflexive action), it was discovered that at least 6 N of force should be applied against the skin to pressurize the body fluid, the entrance of the capillary channel should be recessed between 350 to 600 μm from the tip, and the time of the withdrawal (out) stroke should be longer than the piercing (in) stroke.

An integrated device or system 30 according to one embodiment for achieving rapid sample collection and/or deposition is illustrated in FIG. 1. As can be seen, the system 30 includes a meter 40 with a display 50 for providing analysis results as well as other information, at least one button 60 used to control as well as input data into the meter, and a firing mechanism 70. The meter 40 further incorporates a pressure sensitive trigger 80 that activates the firing mechanism 70 upon pressing the meter at a predefined force against the skin. The example of one such meter and pressure sensitive trigger is described in U.S. Pat. No. 6,319,210 to Douglas et al., which is hereby incorporated by reference in its entirety. The pressure sensitive trigger can be constructed in other manners as well. For example, the pressure sensitive trigger 80 can be mechanical in nature, electrical in nature, or a combination of both. In one variation, the trigger 80 releases a safety that allows the operator to manually fire the firing mechanism 70, and in still yet another embodiment, when the predefined force is applied, the display 50 provides an indicator that the firing mechanism 70 can be fired. The system 30 further incorporates an expression or fluid pressurizing member 90 that is used to pressurize the fluid beneath the skin and an integrated disposable 100 that is used to pierce the skin and analyze the fluid sample. The integrated disposable 100 can be loaded and/or unloaded as well as disposed of as a single unit or in a group, such as in a cartridge, drum, wheel, cassette, and the like. As should be recognized, the meter system 30 can include more or less components and/or be configured differently in other embodiments.

In the illustrated embodiment, the integrated disposable 100 is a micro-sampler, but it should be recognized that certain features can be adapted for use in other types of integrated disposables and devices. An example of the micro-sampler 100 that is used to perform rapid fluid collection will be initially described with reference to FIGS. 2, 3, and 4. As will be recognized, other types of integrated disposables can be modified to incorporate the features from the illustrated micro-sampler 100. Like other types of integrated disposables, the FIG. 2 micro-sampler 100 is typically a single use device that is configured to form an incision, draw a fluid sample, and analyze the collected fluid sample. The micro-sampler 100 is either individually or collectively (e.g., in a cartridge) loaded into the meter 40 or lancing device that subsequently fires the micro-sampler 100 into the skin via the firing mechanism 70. When individually loaded, the micro-sampler 100 is usually unloaded from the meter and disposed of after each test so as to minimize the risk of cross-contamination. When loaded into cartridges, cassettes, drums and the like, the entire cartridge is unloaded and properly disposed of after all or most of the micro-samplers 100 are used. For examples of micro-sampler cartridge designs, please refer to U.S. patent application Ser. No. 11/549,302, filed Oct. 13, 2006, which is hereby incorporated by reference.

Figure 2:
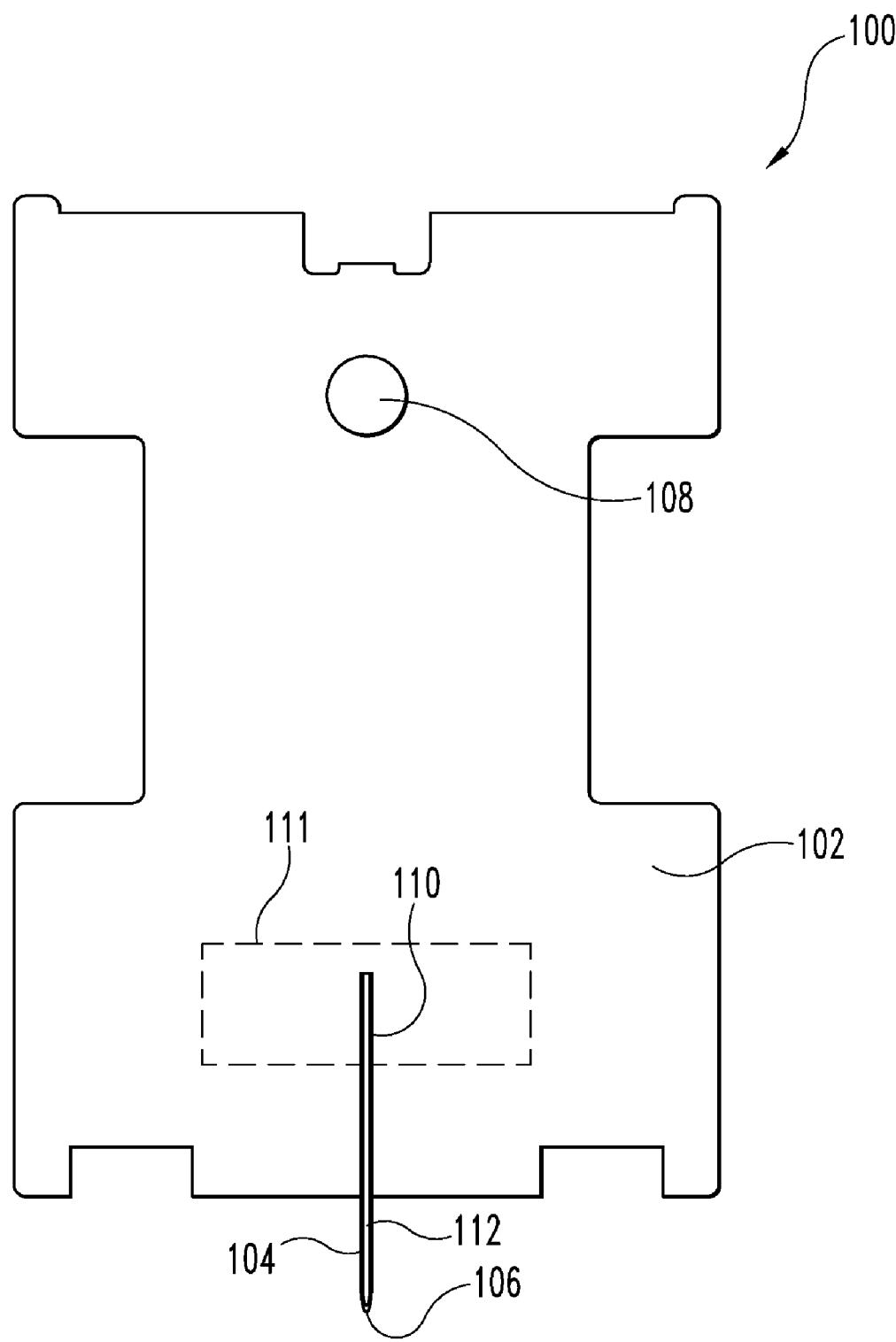
FIG. 2 is an enlarged top plan view of a micro-sampler that is used in the FIG. 1 system.

FIG. 2 shows a top view of the micro-sampler 100. As can be seen, the micro-sampler 100 includes a body portion 102, a shank or shaft portion 104 that extends from the body 102, and a tip 106 at the end of the shaft 104 that is sharpened for cutting incisions. The body 102 has a firing mechanism engagement opening 108 where the firing mechanism 70 of the meter 40 holds the micro-sampler 100 during lancing of the skin or other tissue. As should be recognized, the micro-sampler 100 can be secured to the firing mechanism 70 in other manners or not even mechanically coupled to the firing mechanism but fired indirectly such as through the use of electromagnetic force. The body 102 further has a sample analysis cavity or chamber 110 where the fluid sample is collected and analyzed via a testing device or analysis means 111. The testing device 111 in the micro-sampler 100 can contain the chemistry, such as reagents, enzymes, mediators, etc., as well as other associated components, like electrodes, for analyzing the fluid sample. In another form, the analysis chamber 110 can be also used as a collection point for depositing onto a separate test strip for analysis purposes. Either way, the fluid sample can be analyzed via any number of analysis techniques, such as via electrochemical (e.g., amperometric, coulometric, etc.) and/or photometric analysis techniques, to name a few. The fluid can be rapidly analyzed within less than 10 seconds or even within 0.1-6 seconds. Examples of such rapid analysis techniques are described in U.S. Pat. No. 7,276,146 B2, which is hereby incorporated by reference. With continued reference to FIG. 2, a capillary channel 112 that is configured to move the fluid sample via capillary action extends along the shaft 104 from the tip 106 to the analysis chamber 110 proximal the testing device. While the micro-sampler 100 can be made of various materials, such as metals, ceramics, and/or plastics, the micro-sampler 100 in one embodiment is made of surgical grade stainless steel. Normally, surgical grade stainless steel is hydrophobic, and when hydrophobic, the capillary channel 112 along with the sample analysis chamber 110 can be treated and/or made, entirely or in part, hydrophilic to promote capillary action.

Figure 3:
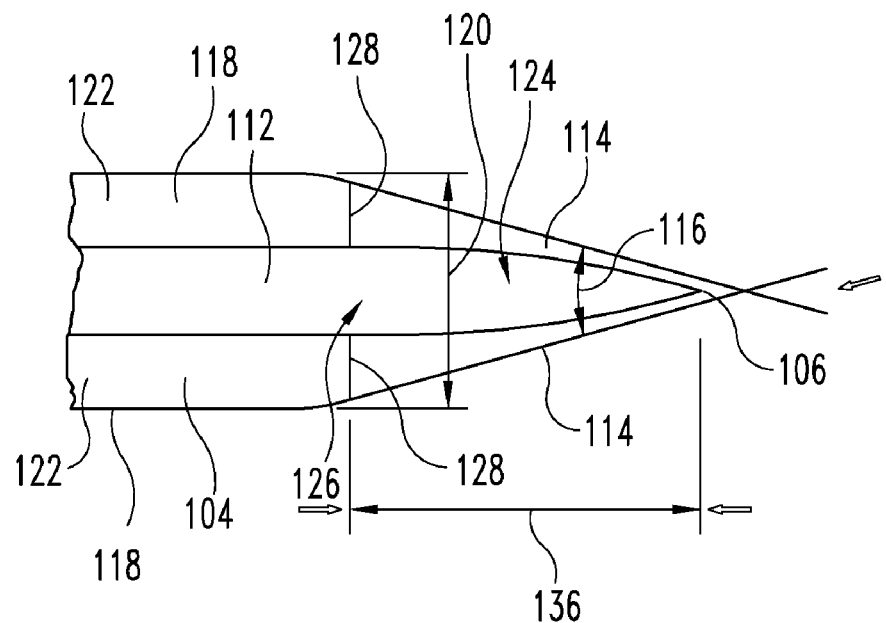
FIG. 3 is an enlarged top view of the tip section of the FIG. 2 micro-sampler.
Figure 4:
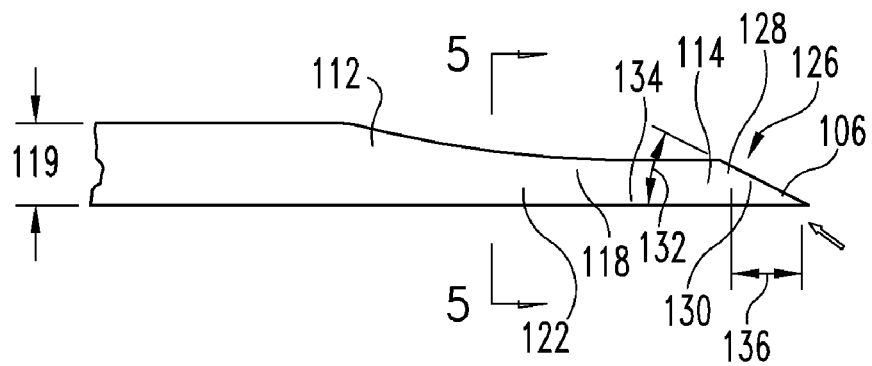
FIG. 4 is an enlarged side view of the tip section of the FIG. 2 micro-sampler.

As noted before, it was discovered that the dimensions and structure of the micro-sampler 100, especially near the tip 106, reduce pain as well as enhance fluid collection by significantly improving collection success rates at relatively short periods of time (before reflexive action takes place). FIG. 3 illustrates a enlarged, top plan view of the shaft 104 near the tip 106 of the micro-sampler 100, and FIG. 4 depicts a side view of the shaft 104 near the tip 106. As can be seen, the micro-sampler 100 has two sharp cutting edges 114 that intersect at the tip 106 to form an included or blade angle 116. In one form, the blade angle 116 is from 20° to 40°, and in one particular form, the blade angle 116 is about 30°. Away from the tip 106, the cutting edges 114 transition into opposing parallel sides 118 of the shaft 104. At the sides 118, the shaft 104 has a width 120 between 300 to 700 µm and in one particular form has a width of about 300 µm. The micro-sampler 100 in one embodiment further has a thickness 119 from 50 to 150 µm and in one particular form has a thickness 119 of about 127 µm.

Looking at FIGS. 3 and 4, the sides 118 of the shaft 104 have sidewalls 122 that define the capillary channel 112. The capillary channel 112 along the sidewalls 122 is treated, coated, and/or otherwise made hydrophilic in order to enhance the body fluid being drawn via capillary action. The capillary channel 112 is sized and configured to draw via capillary action the body fluid sample from the incision site to the analysis chamber 110. With the capillary channel 112 being open, body fluid can be collected along its entire length. This is in sharp contrast to a traditional (closed) hypodermic needle which draws fluid through a single opening. Due to the random distribution of capillaries (or blood vessels) beneath the skin that are cut, blood or other body fluid distribution within the incision may not necessarily be even. In other words, there may be areas along the incision that may supply more fluid than others. With the capillary channel 112 being open, the excess blood from the high supply areas can be wiped or otherwise drawn into the capillary channel 112 along its length during retraction of the micro-sampler 100.

In the depicted embodiment, the sidewalls 122 do not fully extend to the tip 106, but rather, an open section 124 is formed between an opening 126 of the capillary channel 112, as defined by ends 128 of the sidewalls 122 and the tip 106 of the micro-sampler 100. Between the ends of the sidewalls 122 and the tip 106, the micro-sampler 100 has angled wall sections 130 at the open section 124 that extends at an angle 132 relative to an under side 134 of the micro-sampler 100, as is illustrated in FIG. 4. In one form, the angle 132 for the angled wall sections is about 35°. It should be noted that the sidewalls 122 along the capillary channel 112 generally have a sufficient height to draw body fluid via capillary action; whereas, the angled wall sections 130 along the open section 124 generally provide an insufficient contact area to draw fluid via capillary action. That is why the ends 128 of the sidewalls 122 define the opening 126 of the capillary channel 112, and the portion between the ends 128 of the sidewalls 122 and the tip 106 is considered the open section 124. Alternatively or additionally, the open section 124 in another embodiment is hydrophobic or otherwise made to inhibit capillary action along the open section 124. In one form, the open section 124 has a length 136, defined as the distance from the tip 106 to the capillary channel opening 126 (or ends 128), of between 350 to 600 µm, and in one particular embodiment, the channel opening 126 is located about 425 µm from the tip 106. As will be described below, it was unexpectedly discovered that the length 136 of the open section 124 significantly reduced the time needed to successfully collect the fluid sample.

Figure 5:
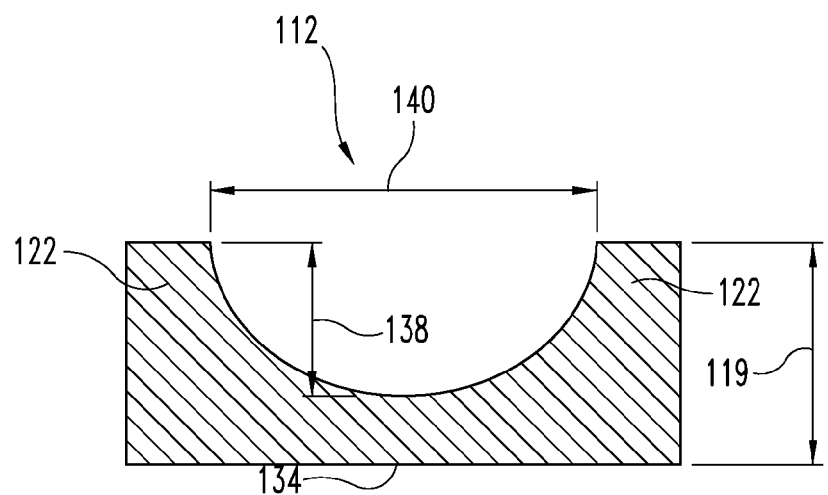
FIG. 5 is a cross-sectional view of the FIG. 2 micro-sampler as taken along line 5-5 in FIG. 4.

As noted before, the capillary channel 112 is hydrophilic and sized to draw the body fluid sample via capillary action from the incision site to the analysis chamber 110. Generally speaking, capillary action is based on the surface tension of the liquid (sample) being drawn along with the adhesive force between the sample and the capillary channel. Specifically, the adhesion of the sample to the walls of the capillary channel 112 causes the edges of the sample to move forward, thereby resulting in a meniscus that is convexly-shaped. The surface tension of the sample keeps the surface intact, so instead of just the edges moving, the entire sample surface moves farther into the capillary channel 112. As should be recognized, the overall contact between the meniscus of the sample and the walls of the channel is one of the factors controlling adhesive force between the sample and the walls, which in turn determines whether or not capillary action takes place as well as the extent and rate of capillary flow. With open capillary channel designs, one of the sides that normally creates the adhesive force in a closed capillary design is removed such that the overall adhesive force between the sample and the walls is reduced. The walls of the capillary channel 112 in the micro-sampler are dimensioned to compensate for this effect so that rapid capillary action can occur. FIG. 5 shows a cross sectional view of the capillary channel 112 as taken along line 5-5 in FIG. 4. The capillary channel 112 has both a depth 138 and a width 140. In one embodiment, the depth 138 is about 0.501 mm and the width is about 0.358 mm. The aspect ratio for the capillary channel 112 is the depth 138 divided by the width 140. In one form, the capillary channel 112 is hydrophilic and has an aspect ratio (depth 138/width 140) between 0.7 to 1.6, and in one particular form, the capillary channel has an aspect ratio of about 1.4. The above-mentioned aspect ratios in open capillary designs were found to promote rapid fluid collection with body fluid samples that have viscosities similar to blood.

Figure 6:
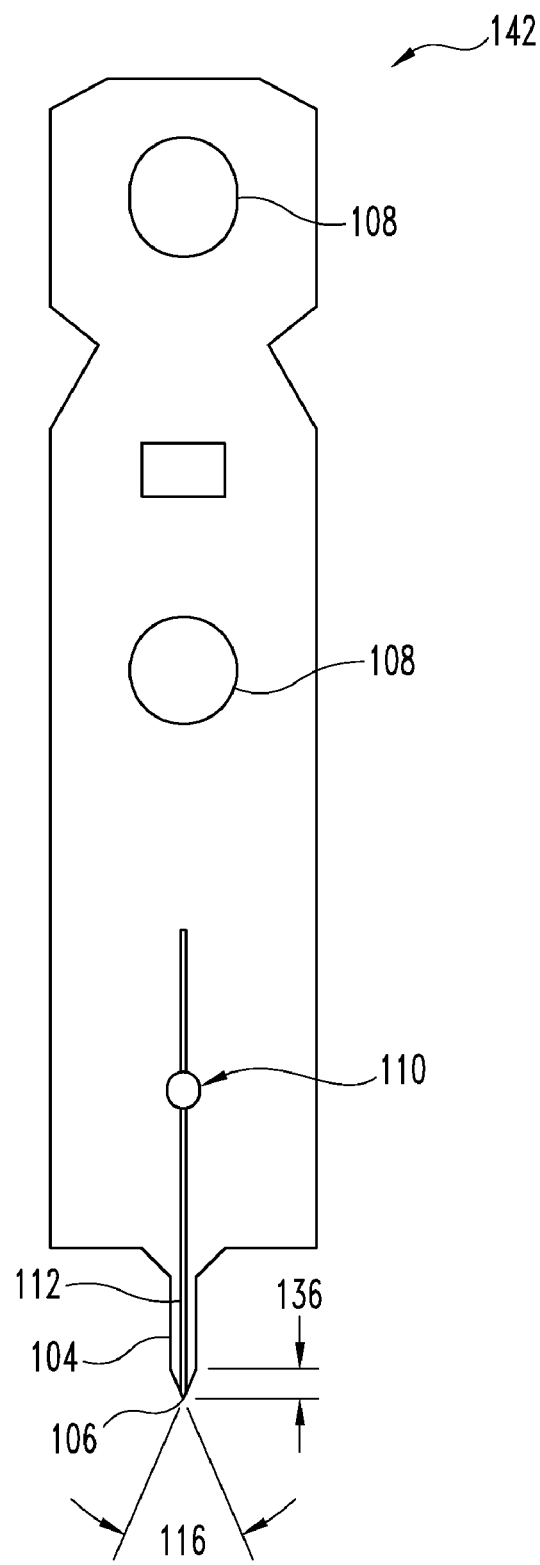
FIG. 6 is a top plan view of a micro-sampler according to another embodiment.

FIG. 6 shows a micro-sampler 142 that shares several features in common with the FIG. 2 micro-sampler 100 like the body, shaft 104, tip 106, and capillary channel 112. The various dimensions and features of the FIG. 6 micro-sampler 142 are the same as those described with reference to FIGS. 3 and 4. The analysis chamber 110 and the overall shape of the body 102, however, are shaped differently than the described before. In particular, the analysis chamber 110 in FIG. 6 is in the form of an opening that allows pooling of fluid on the test element 111. Further, the micro-sampler 142 in FIG. 6 has two firing mechanism engagement openings 108 instead of one so as to provide greater firing stability.

To reduce fluid collection times such that body fluid can be collected before the reflexive action occurs, fluid expression is used to increase the bleeding rate from the incision by pressurizing the fluid around the incision site. During the inventors' investigation, they researched the effects of various types of expression members 90 on the success rate for rapid fluid collection. The findings of the inventors with respect to the various expression members will be discussed at length below. FIGS. 7, 8, 9, 10, and 11 show various other examples of expression members 90 that are used to pressurize the body fluid beneath the skin in conjunction with the system 30 of FIG. 1.

Figure 7:
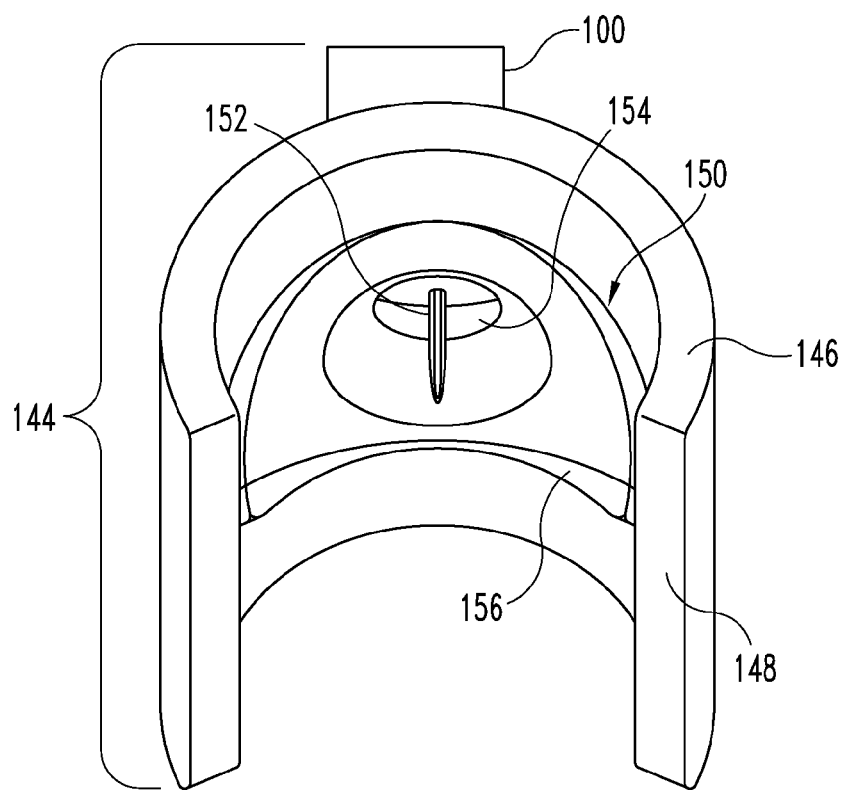
FIG. 7 is a perspective view of an expression assembly that incorporates the FIG. 2 micro-sampler.

FIG. 7 shows an example of an expression assembly 144 that includes the micro-sampler 100 and an expression unit or member 146 that is used to express body fluid. The expression unit 146 has a wrap-around design that allows the unit 146 to wrap around a body part like a finger during fluid expression. As can be seen, the expression unit has a cuff-shaped body 148 extending around a body part receiving cavity 150. An incision site opening 152 is defined in the body 148 that allows the micro-sampler 100 or other incision forming means, such as a lancet or needle, to form the incision. In one form, the incision site opening 152 has an inner diameter from 4.0 to 7.0 mm. Inside the cavity 150, the expression unit 146 has a conical portion 154 surrounding the incision site opening 152. Around the conical portion 154, the expression unit 146 has an isolation ring 156 that promotes confinement of the body fluid around the incision site. In the illustrated embodiment, the isolation ring is saddle-shaped and protrudes from the inner surface of the expression unit 146.

Figure 8:
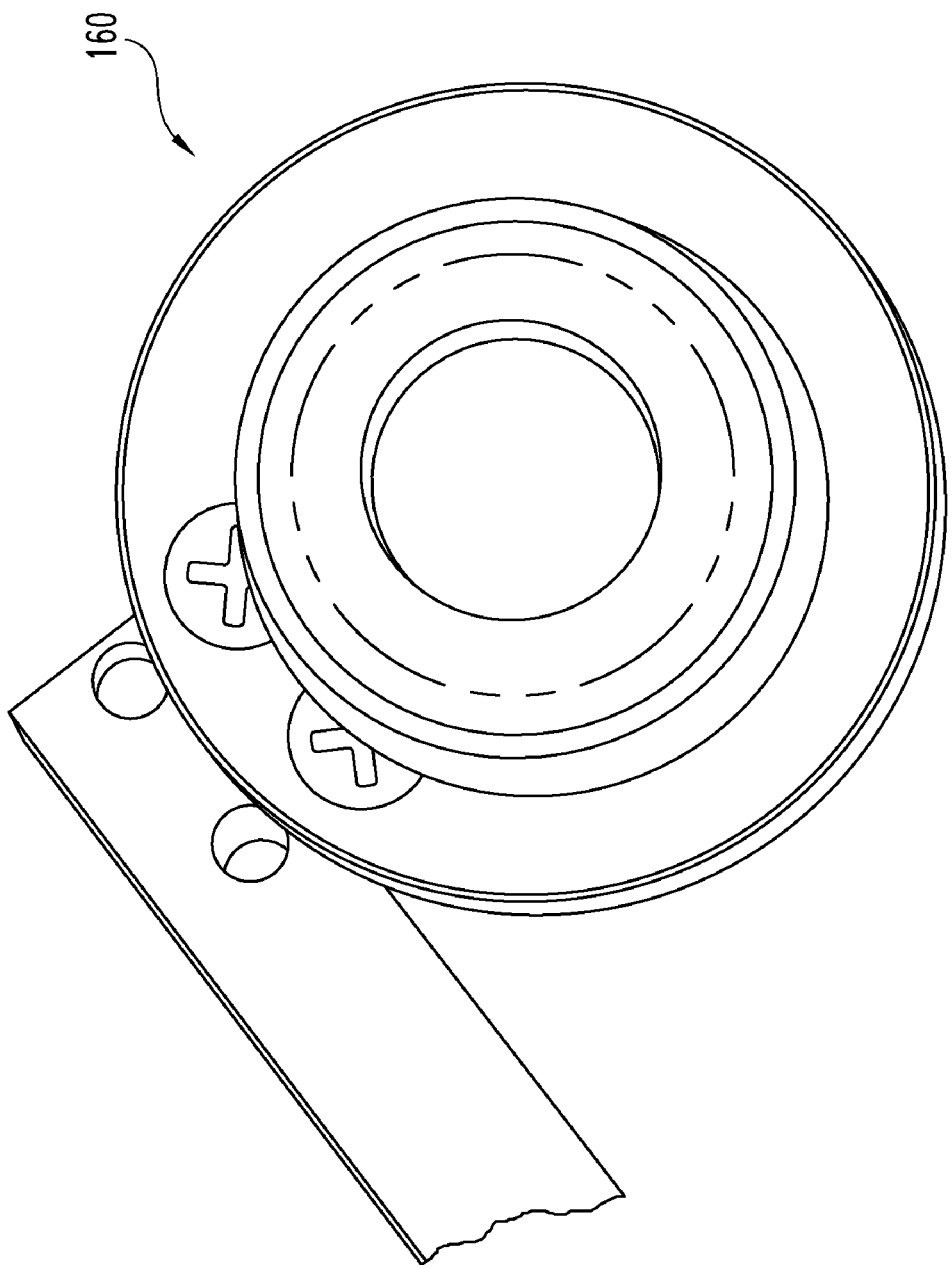
FIG. 8 is a perspective view of an o-ring type expression ring.
Figure 9:
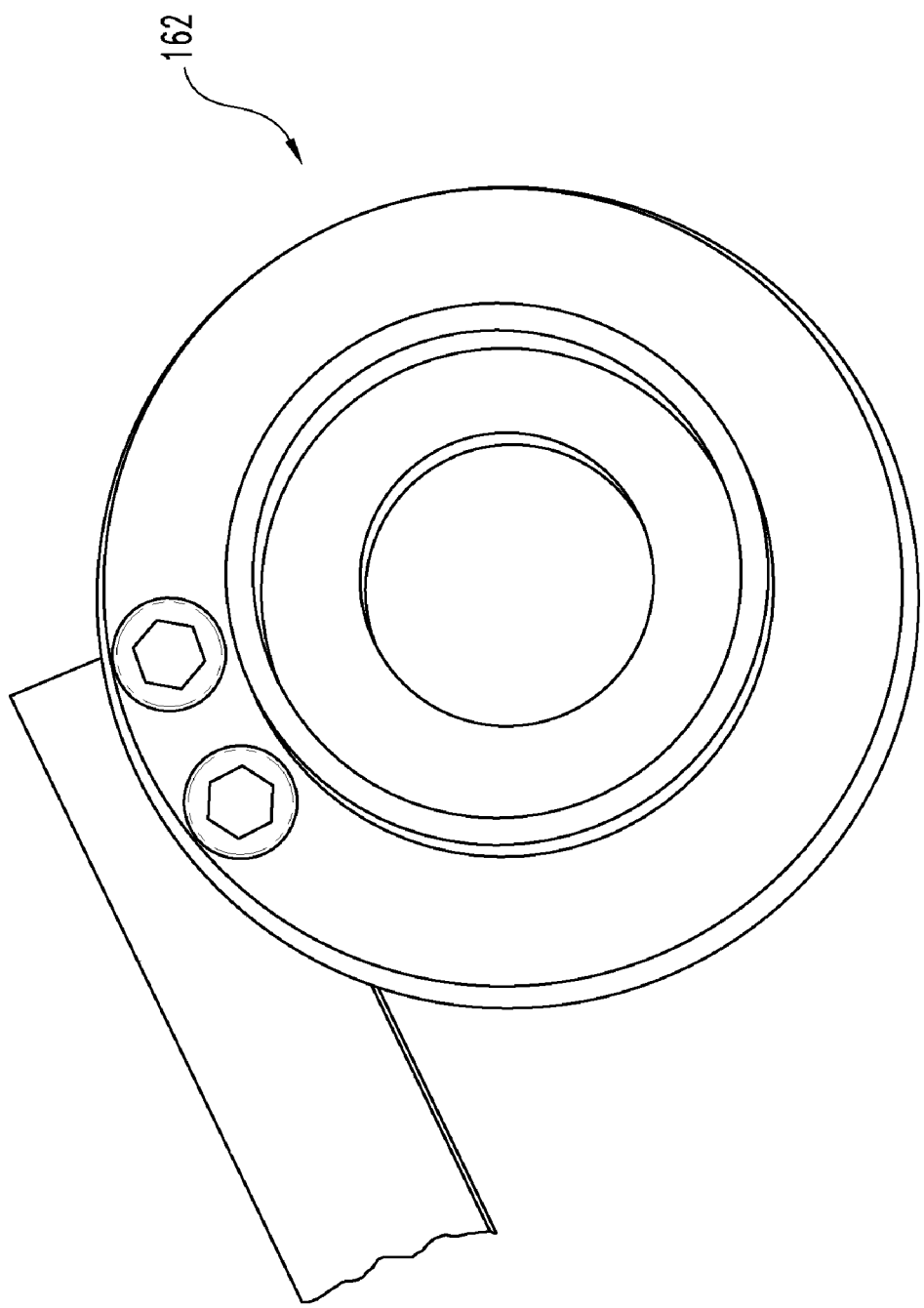
FIG. 9 is a perspective view of a negative sigmoid-type expression ring.
Figure 10:
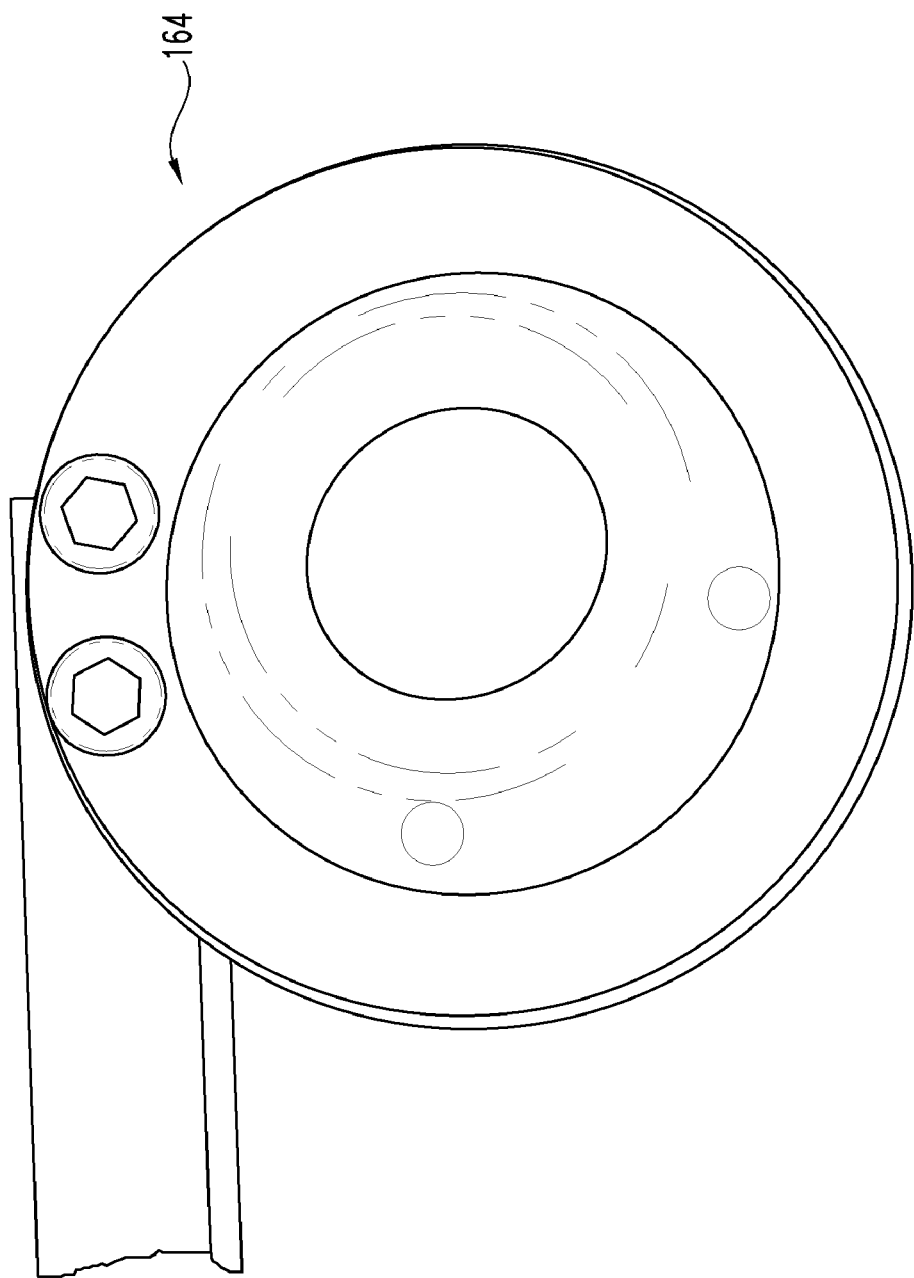
FIG. 10 is a perspective view of a konus-type expression ring.
Figure 11:
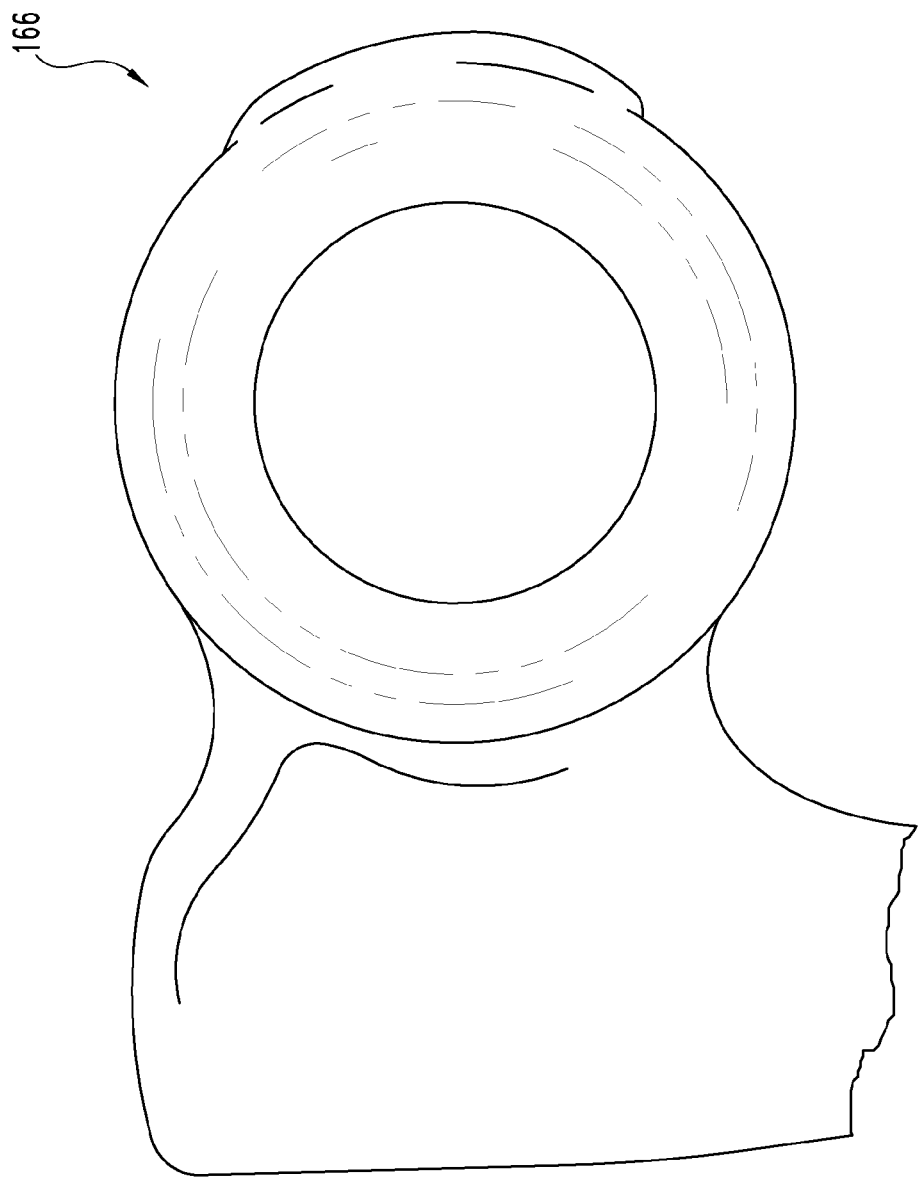
FIG. 11 is a perspective view of a brass expression ring that is over molded with rubber.

FIG. 8 depicts an o-ring type expression member or ring 160 that utilizes an o-ring with a semi-hard material hardness. An example of such an o-ring expression ring is described in U.S. patent application Ser. No. 11/466,202, filed Aug. 26, 2006, which is incorporated by reference in its entirety. FIG. 9 illustrates a negative sigmoid expression ring or member 162 that has a hard material hardness. For further description about the overall shape of the negative sigmoid expression ring 162, please refer to U.S. Patent Application Publication No. 2005/0215923 A1, published Sep. 29, 2005, which is incorporated by reference in its entirety. FIG. 10 shows a "konus" or flexible cone type expression member or ring 164 that is made from flexible or soft material (35 shore A). A brass expression ring 166 that is over molded with rubber is illustrated in FIG. 11 such that the expression ring 166 is generally hard. As should be recognized, the hard expression ring 166 in FIG. 11 can be made from other hard materials, such as steel, iron, etc., as well as covered with other types of elastic materials, such as various plastics. The expression members 90 in FIGS. 8, 9, 10, and 11 all have an inner diameter of 5.5 mm. The outer diameters of the o-ring expression ring 160 in FIG. 8, the negative sigmoid expression ring 162 in FIG. 9, the konus expression ring 164 in FIG. 10, and the hard expression ring 166 in FIG. 11 respectively are 9.8, 10.0, 10.7 and 8.3 mm.

Figure 12:
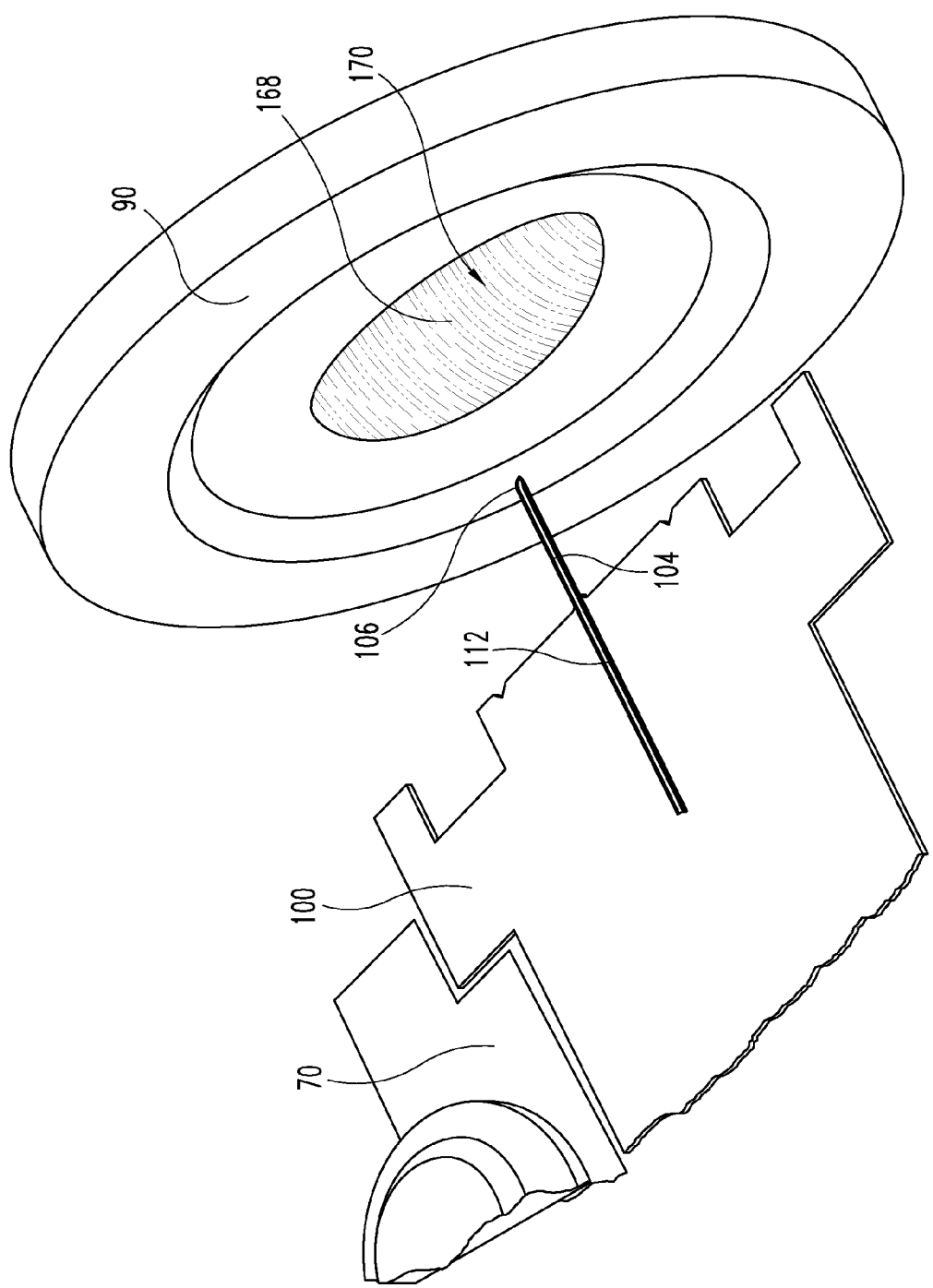
FIGS. 12, 13, 14, 15, 16, 17, and 18 illustrate an enlarged perspective view of the micro-sampler during the various stages for collecting a body fluid sample.
Figure 13:
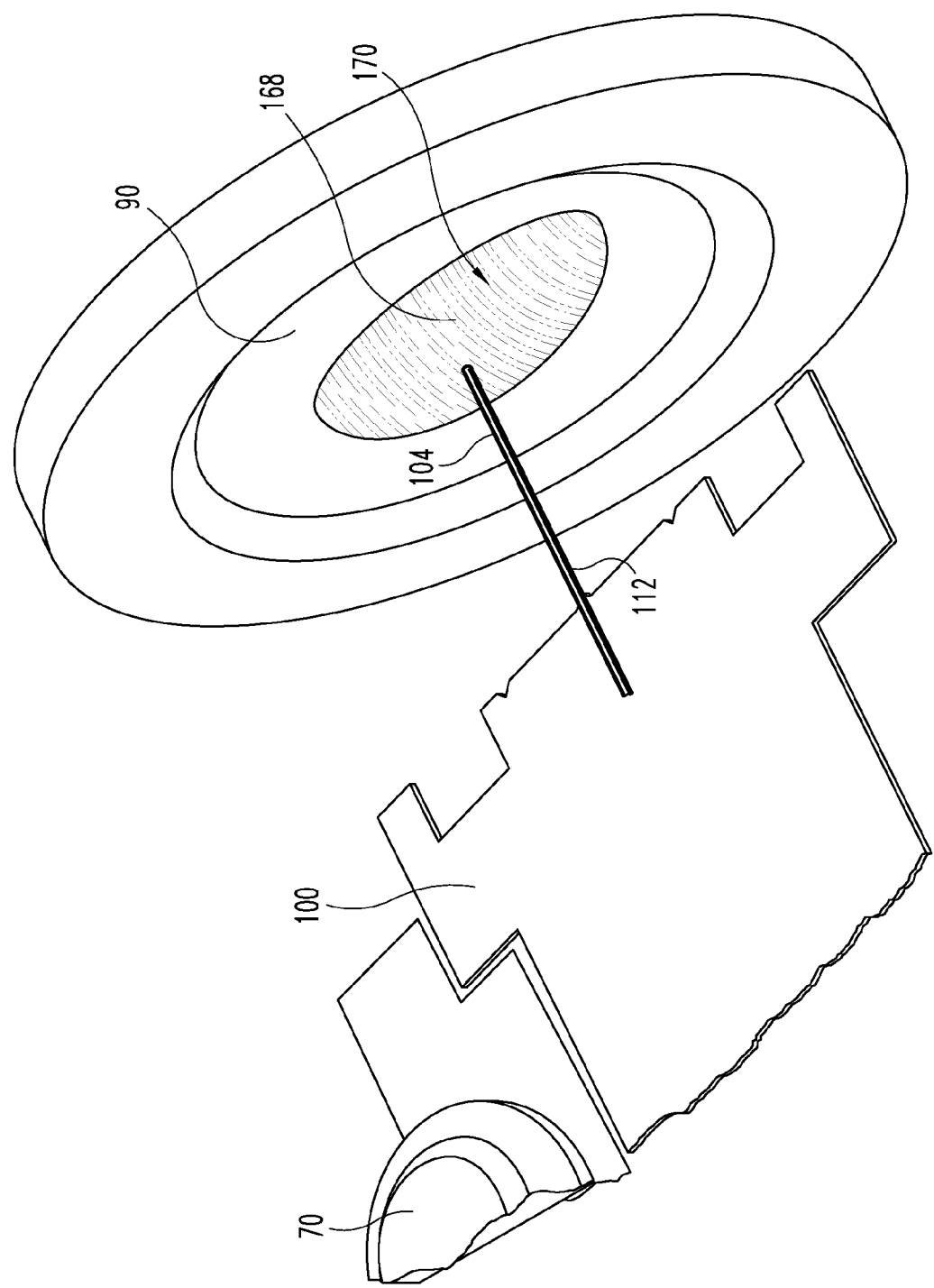

To aid in understanding and appreciation, the overall technique for rapidly collecting a fluid sample will first be described with reference to FIGS. 12 through 18, and then followed by a detailed discussion of the specific variables needed to achieve commercially successful fluid collection before reflexive action occurs. FIGS. 12 through 18 illustrate enlarged perspective views of the micro-sampler 100 during the various stages of fluid collection. The technique for collecting body fluid will be described with reference to collecting body fluid from a finger 168, but it should be recognized that fluid can be collected from other body parts as well. Moreover, the technique will be described with reference to the FIG. 2 micro-sampler 100, but other types of integrated devices or disposables can be used with this technique. Before forming the incision, the expression member 90 is pressed against the finger 168, as is depicted in FIG. 12. The expression member 90 is pressed against the desired incision site 170 on the finger 168 with sufficient force, whereby the expression member 90 defines a perimeter of an isolation region to restrict the escape of blood (and/or interstitial fluid) from the incision site 170 during lancing. The perimeter force is applied by the expression member 90 for a brief period of time to create an isolated perfused area of skin. Looking at FIG. 13, the micro-sampler 100 is fired by the firing mechanism 70 such that the tip 106 extends through the opening of the expression member 90 to cut the skin 168 in a relatively short period of time to a sufficient depth to sever one or more capillaries. In one form, the micro-sampler 100 is fired at a velocity greater than or equal to 1.2 m/s with an optimal velocity of 1.5 m/s. The micro-sampler 100 reaches its maximum penetration depth at or within 5 ms and preferably at or within 3 ms. It was found that such rapid lancing minimized pain.

While some body fluid might collect in the capillary channel 112 during initial penetration, the majority of the fluid is collected after the maximum penetration depth is reached. Upon reaching the maximum penetration depth, the tip 106 of the micro-sampler 100 can remain or dwell at the maximum depth or be partially retracted but still remain beneath the surface of the skin 168. The inventors found that having at least part of the open capillary channel 112 dwell inside the skin for a period longer than the initial penetration of the micro-sampler 100 significantly improved rapid fluid collection. During this dwell time, the micro-sampler 100 can remain stationary or be in the process of being withdrawn from the skin 168.

Depending on the integrated disposable used, fluid collection can occur in several manners. For instance, fluid collection can occur below the skin 168 like a mosquito, above the skin 168 like a vampire bat, or using a combination of both techniques. For example, the previously described micro-sampler 100 is able to collect body fluid below and/or above the skin surface, but in selected embodiments, the micro-sampler 100 generally collects most of the body fluid beneath the skin like a mosquito. The capillary channel 112 in the micro-sampler 100 is open along its length such that the open capillary channel 112 can extend above the skin surface to collect blood (or other body fluid) pooling on the surface of the skin while at the same time drawing blood beneath the skin via capillary action. It is desirable that the sample size is as small as possible for analysis purposes because the smaller sample size permits shallower penetration depths which in turn reduces the pain experienced during lancing. Further, smaller sample sizes typically allow for faster analysis times which is a desirable trait for consumers.

Figure 14:
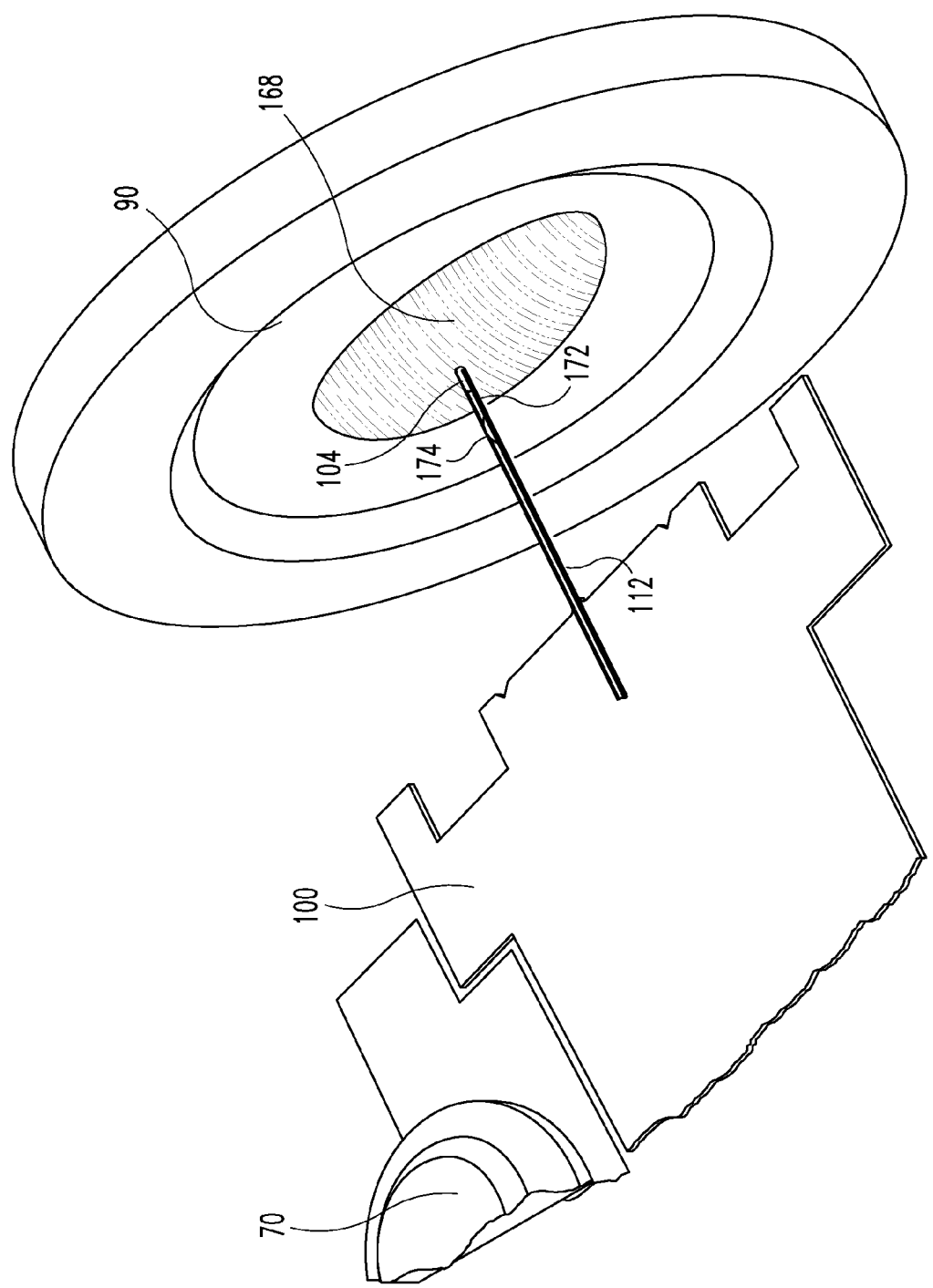
Figure 15:
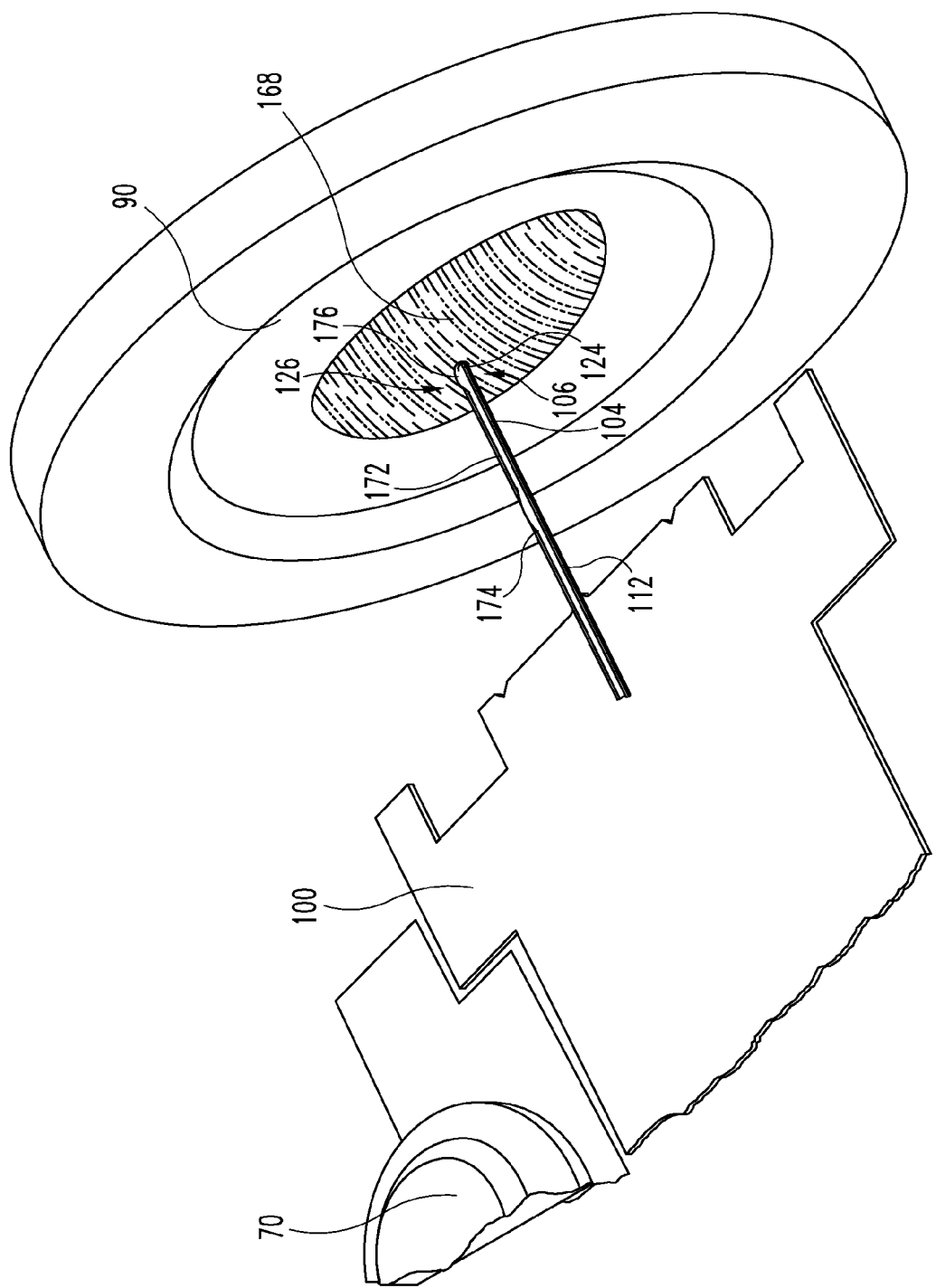

FIG. 14 illustrates body fluid 172 being drawn up the capillary channel 112 while the tip 106 remains beneath the skin 168. Reference number 174 shows the leading edge or meniscus of the body fluid 172 being drawn along the capillary channel 112. As will be explained in greater detail below, some of the body fluid 172 can remain adhered to the micro-sampler 100 outside of the capillary channel 112 at a location where the fluid can later be drawn into the capillary channel 112. One or more drops 176 of body fluid 172 can form on the micro-sampler 100 along the capillary channel 112 and/or on the skin 168. As can be seen in FIG. 15, a single drop 176 forms on the skin 168 along the shaft 104 of the micro-sampler 100 as the tip 106 nears removal from the skin 168. In particular, the drop 176 forms near the capillary channel opening 126. Drops 176 can be formed elsewhere as well. Looking at FIG. 16, a second drop 178 of body fluid 172 (or sometimes even an air bubble) is formed at the transition between the body 102 and the shaft 104 on the micro-sampler 100. To facilitate drop formation, portions of the micro-sampler 100, such as the shaft 104 and/or along the capillary channel 112, can be treated or otherwise made hydrophilic. Other areas of the micro-sampler 100, such as areas where body fluid 172 will not be able to be drawn into the capillary channel 112 and/or at the open section 124, can be treated or otherwise made hydrophobic, thereby inhibiting drop formation at the selected areas.

Figure 16:
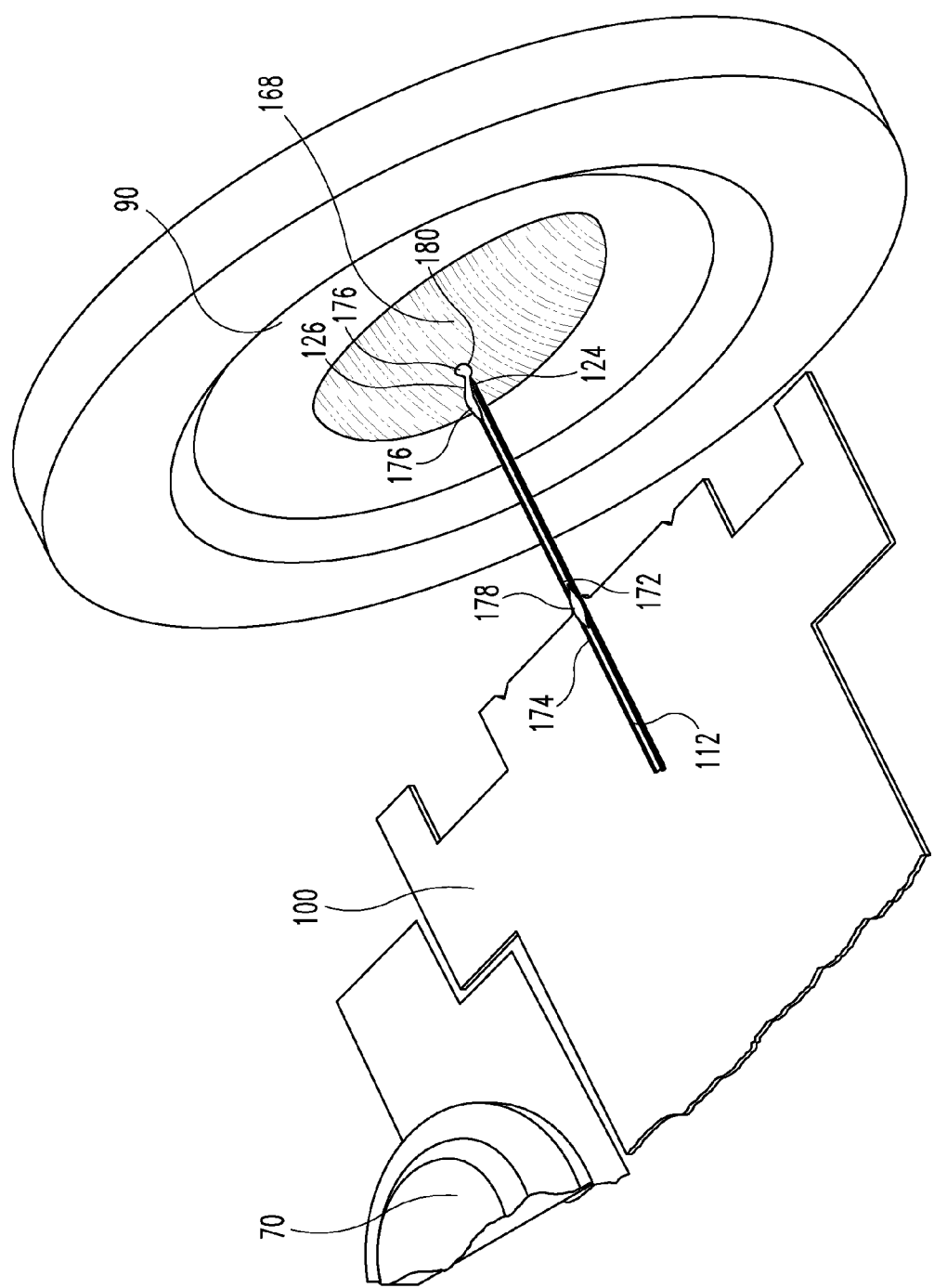
Figure 17:
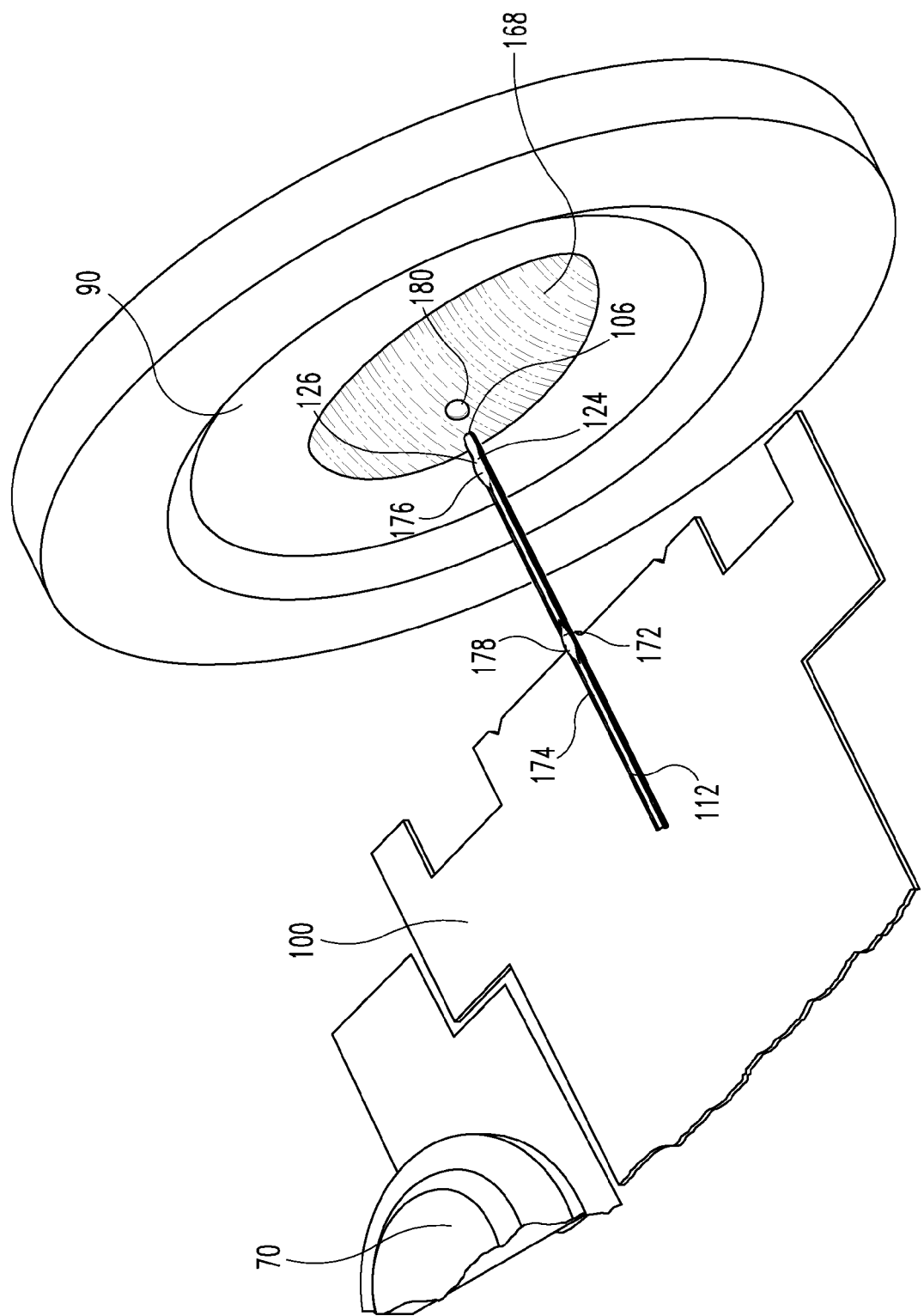

As mentioned before, the particular size of the open section 124 on the micro-sampler 100 was unexpectedly discovered to be a factor for promoting rapid fluid collection. While not absolutely certain, it is thought that the open section 124 might play a role in retaining the drop 176 of body fluid 172 at the capillary channel entrance 126 on the micro-sampler 100 so that the body fluid 172 can be later drawn into the capillary channel 112 after the micro-sampler 100 is removed from the skin 168. Referring to FIG. 16, the drop 176 at the capillary channel entrance 126 separates at the open section 124 from a drop 180 on the skin. It is theorized that the open section 124 allows the drop 176 on the micro-sampler 100 and the drop 180 on the skin 168 to separate without the drop 180 on the skin 168 pulling body fluid 172 from the drop 176 on the micro-sampler 100, as is illustrated in FIGS. 16 and 17. The micro-sampler 100 is completely withdrawn from the skin 168 typically within the reflex reaction time, which is approximately within about 100 to 200 ms, depending on the individual. Upon withdrawal of the tip 106 from the skin 168, the drop 176 remains on the micro-sampler 100 around the capillary channel entrance 126. Before, upon, or after withdrawal of the micro-sampler 100 from the skin 168, the force applied by the expression member 90 can be relaxed.

Figure 18:
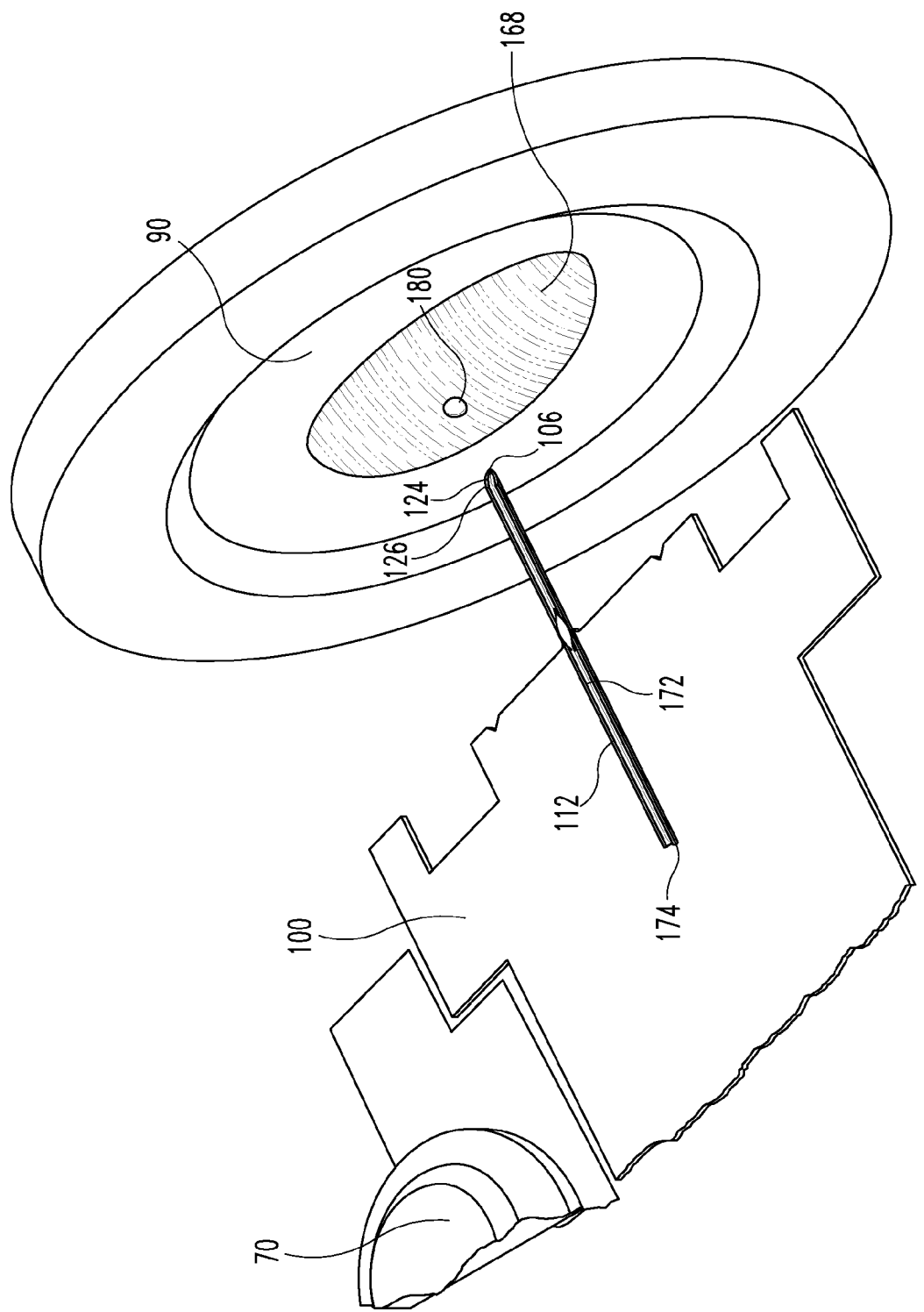

The drops 176, 178 on the micro-sampler 100 form in essence a reservoir on the micro-sampler 100 that allows filling of the capillary channel 112 to continue even after the tip 106 of the micro-sampler 100 is withdrawn from the skin 168. This ability to fill the capillary channel 112 after withdrawal facilitates successful fluid collection even when the micro-sampler 100 penetrates the skin 168 and is withdrawn in a short period of time, such as before reflexive action occurs. FIGS. 17 and 18 illustrate how the drops 176, 178 of body fluid 172 on the micro-sampler 100 complete filling of the capillary channel 112. As seen by the leading edge 174 of the body fluid 172 in FIG. 17, the body fluid 172 does not yet completely fill the capillary channel 112, but the drop 176 (as well as drop 178) provides a reserve of body fluid 172 that can be drawn into the capillary. FIG. 18 shows that the body fluid 172 that once formed the drop 176 at the capillary channel entrance 126 fills the capillary channel 112 such that the leading edge 174 of the body fluid 172 is located at the end of the capillary channel 112.

In all of the above-discussed drawings (FIGS. 12-18), the testing device 111 has not been shown so that the body fluid 172 filling the capillary channel 112 can be easily viewed. It should be appreciated that the body fluid 172 can start depositing onto the testing device 111 when the capillary is partially or fully filled. In one embodiment, the capillary channel 112 has a volume that is equal to or greater than the volume required for accurate testing, and the micro-sampler 100 is configured to deposit fluid onto the testing device 111 only after the capillary channel 112 is filled with body fluid 172.

As mentioned before, the inventors discovered that one source for inaccurate test results in samples in the sub-microliter or nanoliter range is caused by the evaporation of the sample during fluid collection as well as analysis. In these tiny test volumes, even slight variations in volume can create significant differences in analyte concentration measurements. It should be appreciated that the capillary channel 112 in the micro-sampler 100 has an open design that is prone to evaporation. This issue of evaporation from such open capillary channels is addressed by drawing and depositing the sample on the sample analysis device 111 within 500 ms of piercing the skin. In other aspects, the fluid is deposited within 150 or 200 ms to further reduce evaporation, and in a further aspect, the fluid is deposited within 100 ms and even 75 ms which provides further benefit. By depositing the collected fluid in such a rapid fashion, only minimal evaporation can occur, thereby leading to more accurate results. The above-mentioned times are measured from initial penetration of the micro-sampler 100 into the skin 168. In one embodiment, the measurement of these times is stopped once a sufficient amount of body fluid for testing purposes is deposited onto the test device 111. This end time can be sensed through the use of drop detectors and the like within the micro-sampler 100. It should be recognized that the rapid deposition can be measured or based on other periods. For instance, the deposition time could be based on how long the sample is exposed to air before being deposited on and/or absorbed into the testing means.

One factor mentioned before for achieving successful fluid collection before reflexive action occurs is the lancing or piercing profile used to extend and retract the micro-sampler 100 during incision formation. It was discovered that the profile should include a relatively quick piercing or extension phase followed by a relatively long withdrawal phase of the micro-sampler 100 from the skin. The quick penetration stroke is thought to reduce pain as well as increase the time available for the withdrawal stroke, while the longer withdrawal stroke increases residency time of the capillary channel 112 beneath the skin which is thought to increase the amount of fluid collected.

Figure 19:
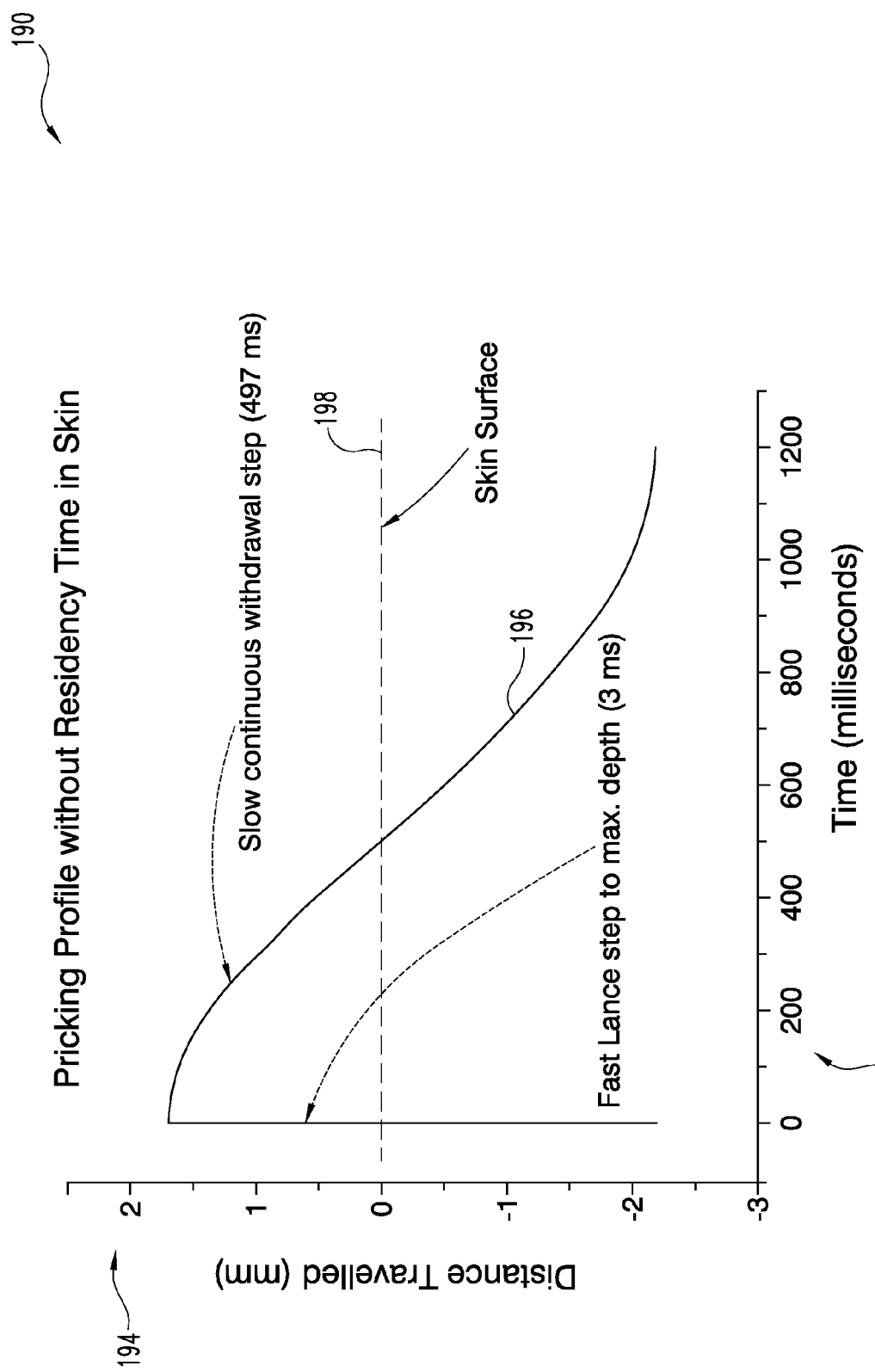
FIG. 19 is a graph that illustrates a lancing profile with a slow continuous withdrawal phase according to one embodiment.

FIG. 19 shows a graph 190 that illustrates the lancing profile for micro-sampler 100 according to one technique that samples the fluid in a rapid manner. X-axis 192 in the graph 190 represents the time, and Y-axis 194 represents the travel distance of the tip 106 of the micro-sampler 100. Profile line 196 illustrates the lancing profile of the micro-sampler 100, and dashed line 198 represents the skin surface. As can be seen, the micro-sampler 100 is fired and reaches its maximum penetration depth within 3 milliseconds (ms). Once the maximum penetration depth of the tip 106 is achieved, which in this example is about 1.6 to 1.7 mm, the micro-sampler 100 starts to be withdrawn at generally a constant rate. In other words, the tip 106 of the micro-sampler 100 in this example generally does not dwell or reside at the maximum penetration depth before being retracted from the skin. In the illustrated case, the tip 106 is withdrawn at a generally continuous rate for about 497 ms before being withdrawn from the skin, giving a total dwell time within the skin of about 500 ms. As the tip 106 of the micro-sampler 100 withdraws within the skin, the micro-sampler 100 collects body fluid, and even once removed from the skin, the micro-sampler 100 is able to collect fluid from the surface of the skin for at least a short distance.

Figure 20:
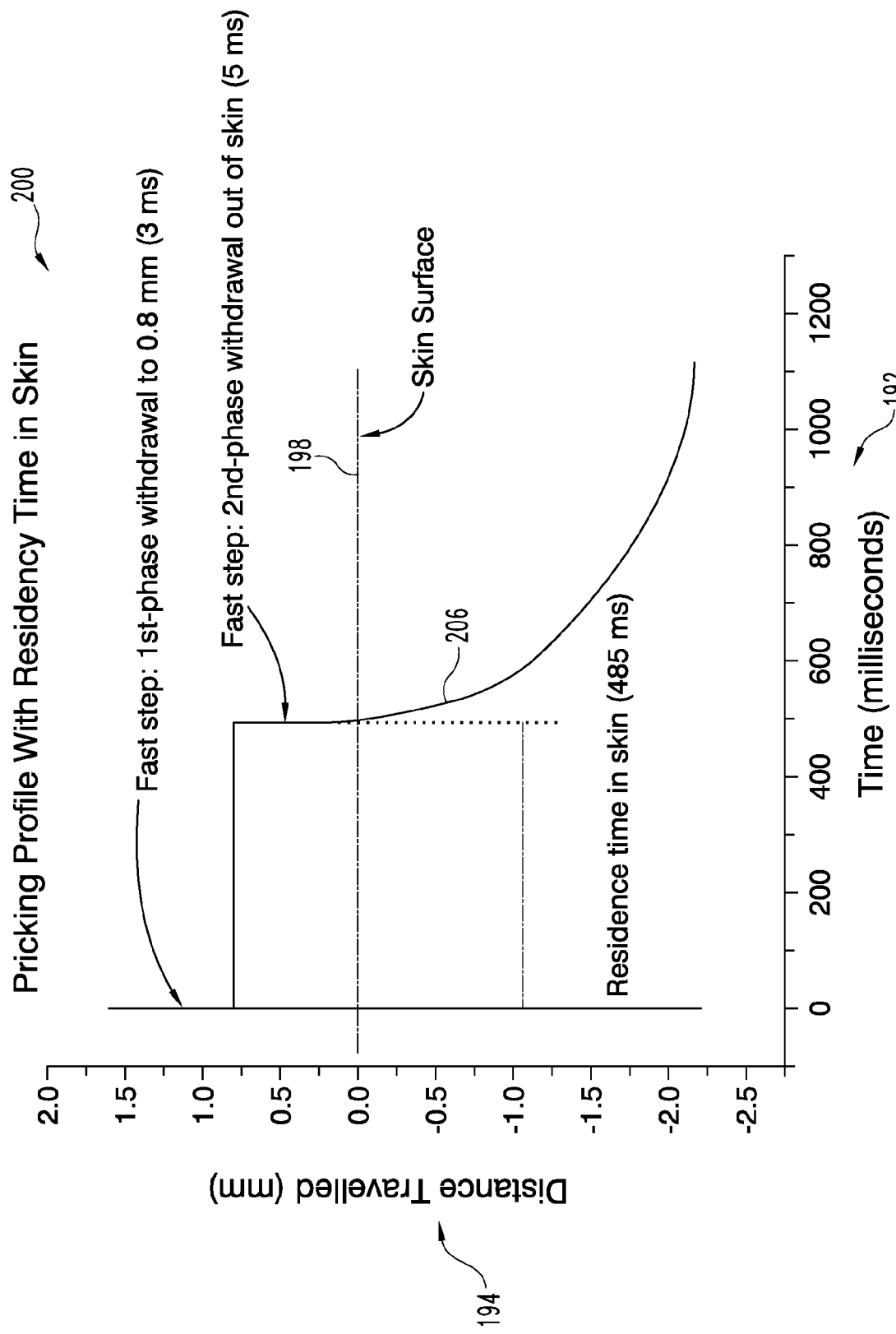
FIG. 20 is a graph that illustrates a lancing profile with a residence phase according to another embodiment.

FIG. 20 shows a graph 200 that illustrates the lancing profile for micro-sampler 100 according to another technique that samples the fluid rapidly. Profile line 206 illustrates the lancing profile of the micro-sampler 100, and dashed line 198 represents the skin surface. As can be seen, the tip 106 of the micro-sampler 100 reaches maximum penetration depth of about 1.6 to 1.7 mm, and withdrawn to about a 0.8 mm depth within 3 ms. It is theorized that the partial withdrawal of the tip 106 promotes pooling of the body fluid within the incision which in turn can be collected by the capillary channel 112. The tip 106 of the micro-sampler 100 dwells at the 0.8 mm depth to collect fluid for about 477 ms, and then the tip 106 of the micro-sampler 100 is rapidly removed from the skin within about 5 ms. The total dwell time of the micro-sampler 100 within the skin is approximately 485 ms in this example. It is thought that the fast lance, partial withdraw, long dwell, and fast full withdraw steps in the technique illustrated in FIG. 20 promoted successful rapid fluid collection. It should be appreciated that the specific times can vary in the other examples.

In one experiment, the success rate of filling a micro-sampler was evaluated on twenty subjects involving 140 sticks per micro-sampler design. Three types of micro-samplers designs were used: designs A, B, and C. In the actual experiment, micro-sampler designs A, B, and C were respectively referred to as micro-sampler designs "87", "88" and "89." Micro-sampler designs A, B, and C were similar to the micro-sampler 100 illustrated in FIGS. 2, 3, 4, and 5. However, the length 136 of the open section 124, as defined by the distance from the tip 106 to the capillary channel opening 126, varied in these designs (see, FIG. 3). In particular, the lengths 136 of the open section 124 for micro-sampler designs A, B, and C were 382, 425 and 573 µm, respectively. In the experiment, capillary channels 112 having lengths of 4.5 mm and 8.6 mm were tested. Filling was considered successful when the entire length of the capillary channel 112 was filled with the body fluid, which in this case included blood. As should be recognized, if nearly the entire length of the capillary channel 112 was not filled, then the blood would not be able to be deposited into the analysis device 111.

Figure 21:
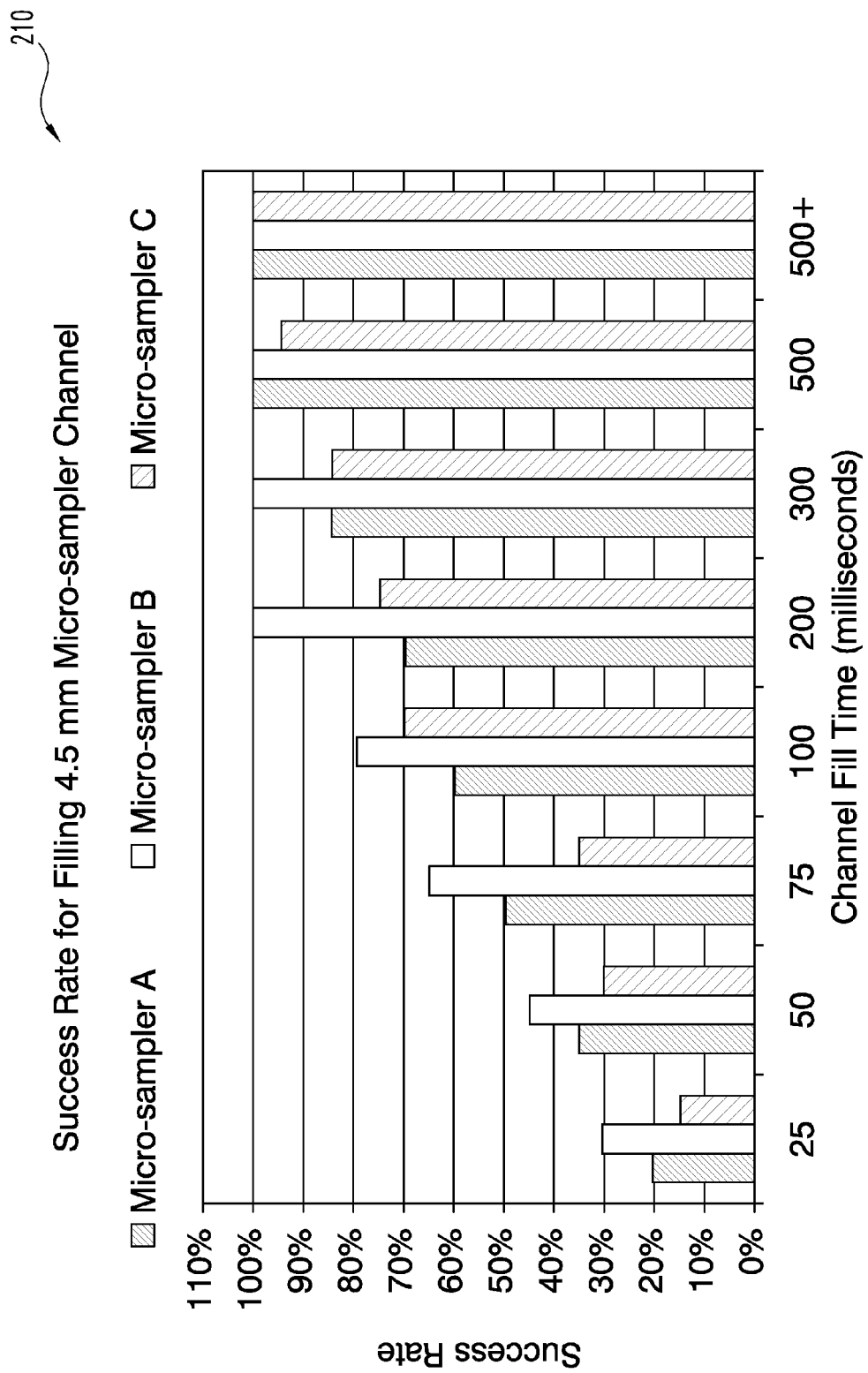
FIG. 21 shows a success rate graph for an experiment conducted with the FIG. 2 micro-sampler.

All subjects were lanced to the same depth of 1.6 mm. In the experiment, the expression assembly 144 (or sometimes referred to as a "konus") applied 10 N force on the subject's finger for fluid expression purposes. The force was applied to the finger with the expression unit 146 before the incision was formed in order to pressurize the fluid within the skin. This force was continuously applied as the incision was cut and during sample collection. The previously-described graph 190 in FIG. 19 shows an example of the pricking profile used in the experiment. The lance portion of the profile was relatively fast and constant, and the withdrawal of the micro-sampler 100 was relatively a slow, continuous single phase step. In one example, the speed of the micro-sampler 100 at initial contact was greater than or equal to 1.3 m/s, and the tip 106 of the micro-sampler 100 reached the maximum penetration depth of 1.6 mm within 3-5 ms. The withdrawal time varied from 25 milliseconds to 500 milliseconds. In all instances of the experiment, full withdrawal of the micro-sampler out of the skin occurred in less than 1000 ms. Table 1 below illustrates the success rates for filling 4.5 mm and 8.6 mm long capillary channels 112 with micro-sampler designs A, B, and C. Graph 210 in FIG. 21 illustrates an expanded view of the same data for the design having the 4.5 mm long capillary channel 112. It should be noted that the "Channel Fill Time" in the FIG. 21 graph 210 is the same as the "Withdrawal Time" indicated in Table 1 below. It also should be noted that the withdrawal times are based on the total time elapsed to that point such that it includes both the time needed to reach maximum penetration depth plus the time required to withdraw the micro-sampler 100 from the skin. For example, the 500 ms withdrawal time in Table 1 below includes 3 ms required to reach the maximum penetration depth along with 497 ms needed to withdraw the micro-sampler 100 from the skin.

TABLE 1

| | | Success Rate of Channel Filling | | | |
|---|---|---|---|---|---|
| | | 4.5 mm Channel | | 8.6 mm Channel | |
| Micro-sampler | Channel Entrance to Tip (µm) | Withdrawal time (ms) | Success Rate (%) | Withdrawal time (ms) | Success Rate (%) |
| A | 382 | 500 | 100 | 500 | 95 |
| B | 425 | 200 | 100 | 300 | 100 |
| C | 573 | 500 | 95 | 500 | 85 |

It was unexpectedly found that the length 136 of the open section 124 dramatically improved the success rate for relatively short fluid collection times. As can be seen in FIG. 21, a success rate of 100% (n=140 sticks) capillary fill was achieved with micro-sampler design B (the open section 124 having 425 µm length 136) for a 4.5 mm long capillary channel with the expression unit 146 applying a 10 N force on a finger and a pricking profile with a withdrawal time of 200 ms. In comparison with the other designs, the micro-sampler B design achieved a 100% fill success rate in a considerably shorter period of time. With the 100% channel filling success rate for both the incision forming and sample collection steps, the only variable controlling the success rate for the overall test is the reliability of the test strip (or other testing means) used to analyze the fluid sample. The significance of this 100% sample collection success rate is that the overall success rate for the micro-sampler would be comparable to or even the same as today's (or even future) test strips.

With the design being integrated such that all of the steps are performed quickly, it is expected that the overall test success rate might be even better than traditional designs because of less manual handling by the user. With traditional (non-integrated) test strips, the fluid sample size is somewhat limited by the hand-eye coordination and motor skills of the user. If the drop of blood is too small, the user will not be able to properly position the test strip to collect the blood or other fluid sample. With the advent of test strip technology permitting smaller sample sizes, the limiting factor will become the user's ability to collect the sample. As should be recognized, the smaller sample sizes can be obtained at shallower penetration depths which in turn results in less pain for the user. Likewise, the speed at which the sample is collected and analyzed will be limited to the user's ability to collect the sample and load the test strip into the meter. The quicker the test can be completed, the more convenience for the user because the user wastes less time taking tests.

Variations in skin properties, such as skin elasticity, can change the actual penetration depth into the skin. For example, the firing mechanism 70 is set to 1.6 mm, but the actual penetration depth might in actuality be 1.2 mm. In this regard, a second study was performed on two individuals that compensated for skin variation. In other words, the skin penetration depth was precisely controlled or calibrated for the individual. The lancing depth in this experiment was originally set to 1.6 mm. The subject was lanced and fluid was collected. The expression unit 146 of the type described above was used to apply force to the skin of between 4 to 10 N to the finger before the skin was punctured and until the sample was collected. The lancing profile illustrated in the FIG. 19 graph 190 was used during the experiment (i.e., fast-in to maximum depth and a relatively slow continuous withdrawal out of skin). If 300 nl of fluid was collected, the setting on the firing mechanism was reduced by half and the fluid collection process repeated until the minimum depth was established at which 300 nl could be consistently collected.

The minimum or calibrated depth setting was then used to collect fluid from the individual subjects. Tables 2 and 3 below show success rates in this experiment for filling an 8.6 mm channel with micro-sampler designs A and B, respectively.

TABLE 2

Micro-sampler Design A

| Force Applied by Expression Unit on Skin | % Success Rate for Capillary Fill (8.6 mm) Withdrawal time from maximum depth (milliseconds) | | | | |
|---|---|---|---|---|---|
| | 75 | 100 | 250 | 500 | 1000 |
| 4 | — | 0 | 0 | 100 | 100 |
| 5 | — | 0 | 50 | 100 | 100 |
| 6 | 0 | 0 | 100 | 100 | 100 |
| 10 | 100 | 100 | 100 | 100 | 100 |

TABLE 3

Micro-sampler Design B

| Force Applied by Expression Unit on Skin | % Success Rate for Capillary Fill (8.6 mm) Withdrawal time from maximum depth (milliseconds) | | | | |
|---|---|---|---|---|---|
| | 75 | 100 | 250 | 500 | 1000 |
| 4 | — | 0 | 33 | 100 | 100 |
| 5 | — | 50 | 100 | 100 | 100 |
| 6 | 50 | 83 | 100 | 100 | 100 |
| 10 | 100 | 100 | 100 | 100 | 100 |

As can be seen in Tables 2 and 3, a 100% success rate was achieved for a 8.6 mm channel fill (or less) with at least 10 N expression force and a 75 ms withdrawal time with both micro-sampler designs A and B. At the 75 ms withdrawal time, fluid collection can occur before the reflexive action of the individual. In comparison to design A, the micro-sampler B design had improved fluid collection success at the other withdrawal times.

Figure 22:
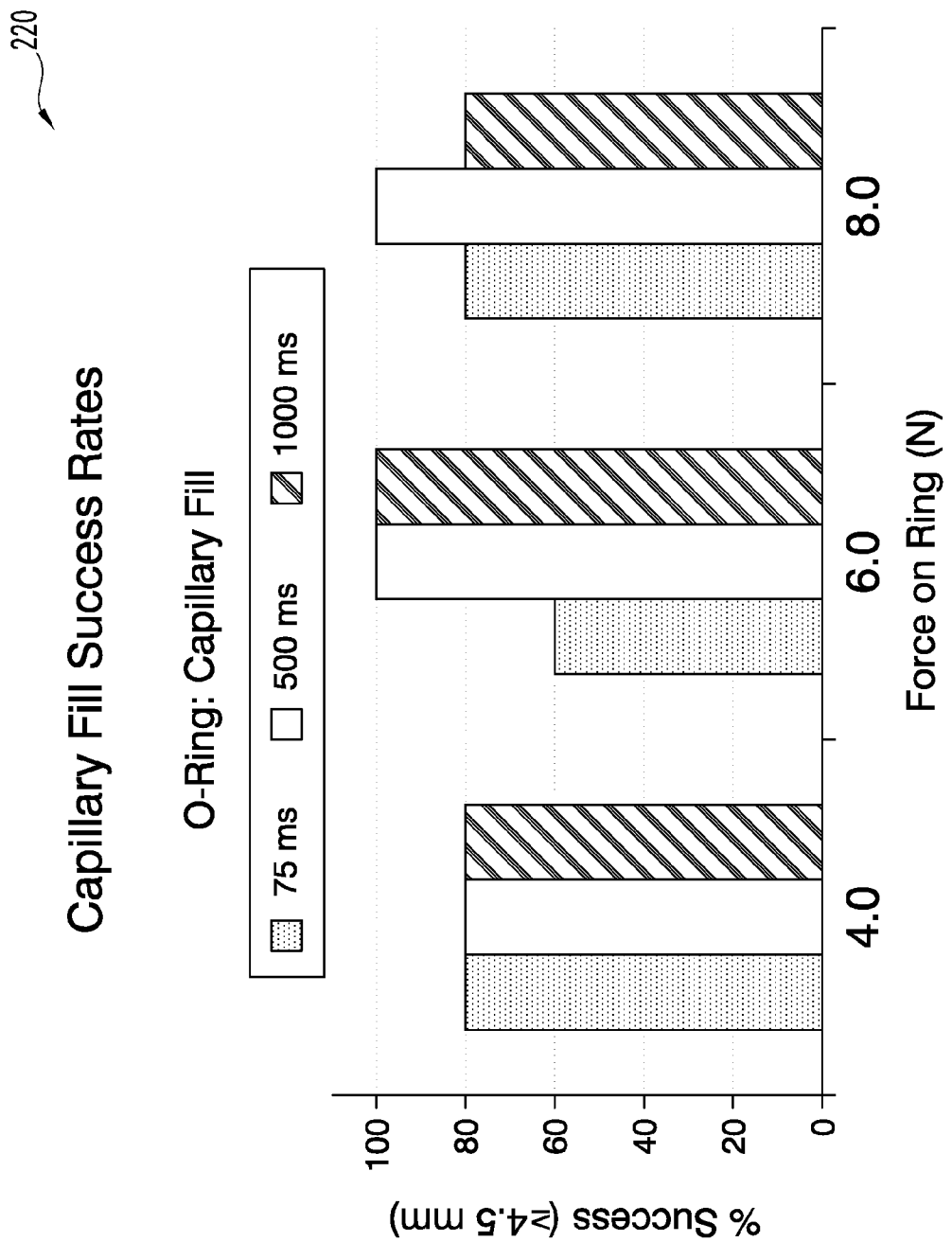
FIG. 22 shows a success rate graph for an experiment conducted with the o-ring type expression ring of FIG. 8.
Figure 23:
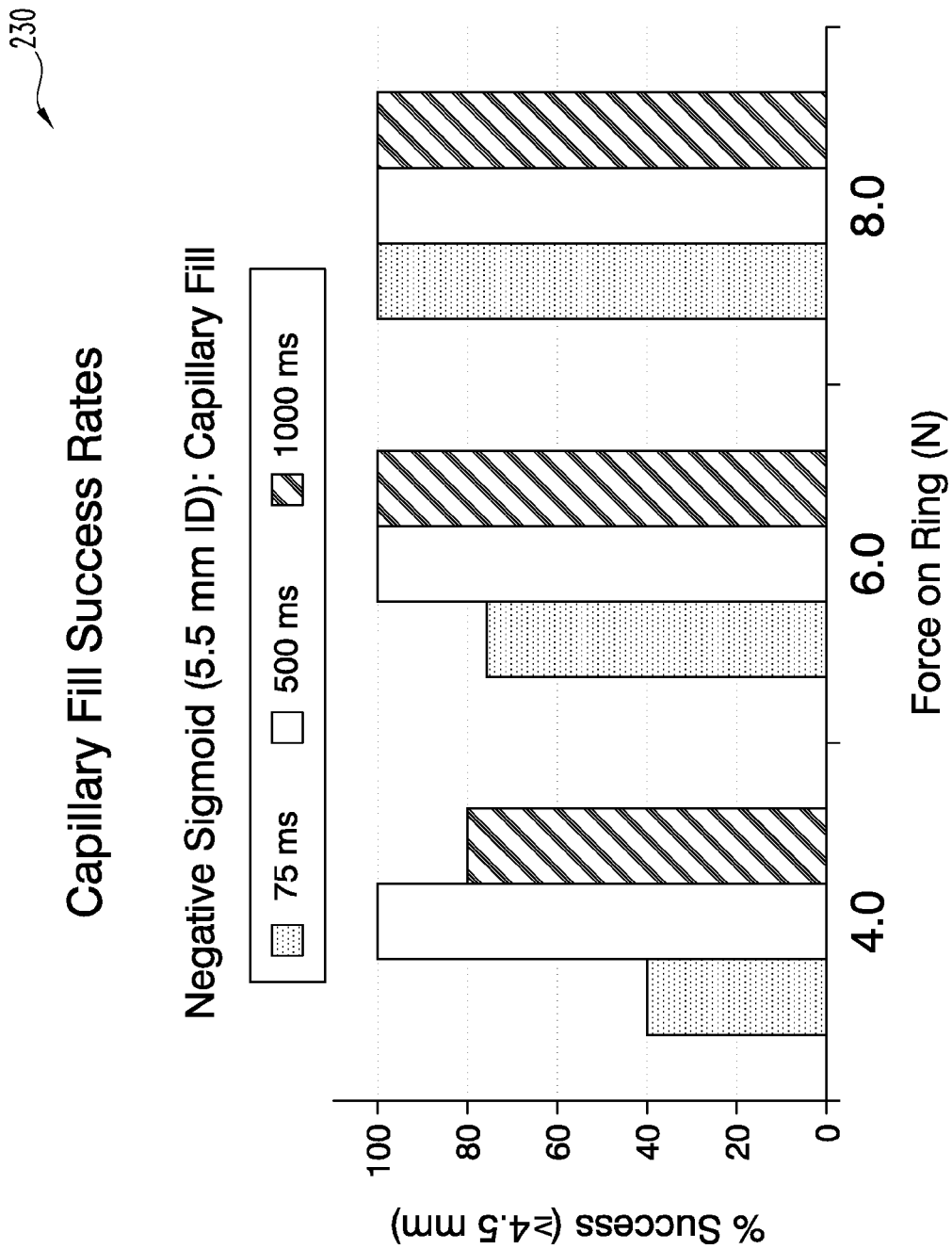
FIG. 23 shows a success rate graph for an experiment conducted with the negative-sigmoid type expression ring of FIG. 9.
Figure 24:
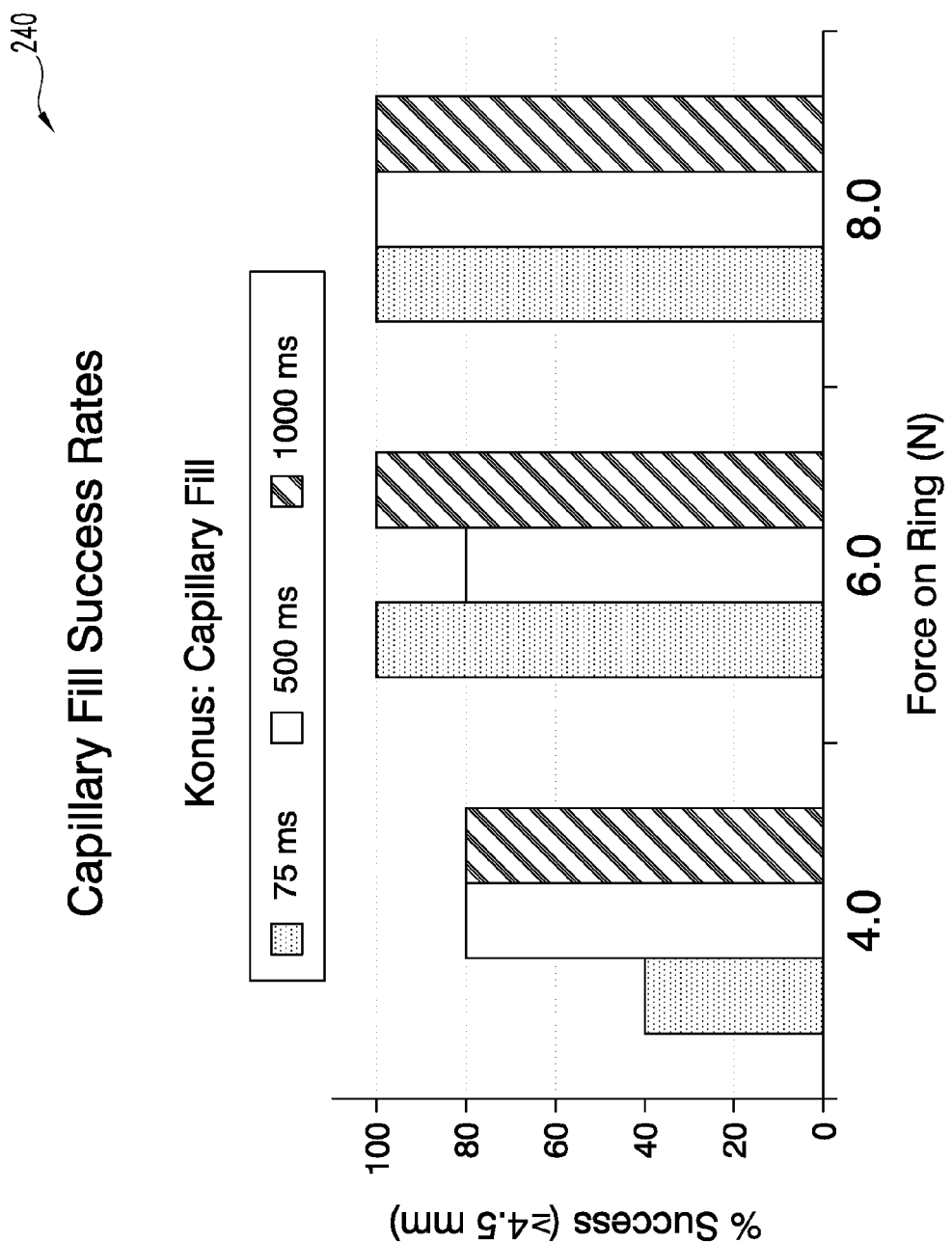
FIG. 24 shows a success rate graph for an experiment conducted with the konus type expression ring of FIG. 10.
Figure 25:
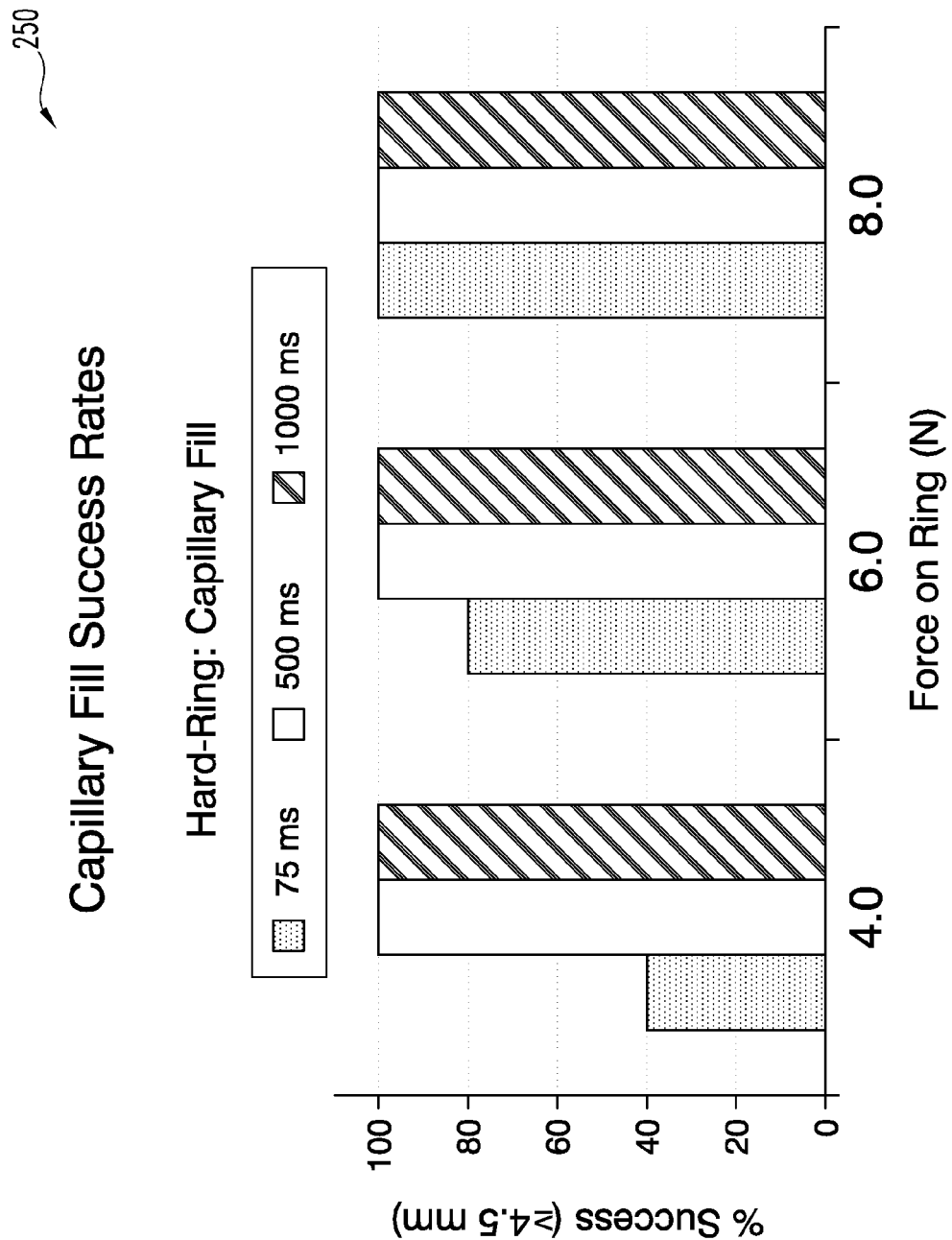
FIG. 25 shows a success rate graph for an experiment conducted with the hard-ring type expression ring of FIG. 11.

Further experiments were conducted in order to determine the minimal force that could be applied by the expression against the skin that still achieved successful rapid fluid collection. The expression units 90 illustrated in FIGS. 8, 9, 10, and 11 were tested at different force levels for the micro-sampler design B. Specifically, 4.0, 6.0, and 8.0 N were applied by each expression unit 90 against the skin. Further, the total dwell time of the micro-sampler 100 beneath the skin (from initial penetration to complete removal) was tested at three different times: 75 ms, 500 ms, and 1000 ms. The lancing profile 196 of the graph in FIG. 19 was used during fluid collection. In each test, capillary channel filling was considered successful when at least 4.5 mm length of the capillary channel 112 was filled. Graph 220 in FIG. 22 illustrates the test results for the o-ring type expression member 160 illustrated in FIG. 8. In FIG. 23, graph 230 depicts the test results for the negative sigmoid expression member 162 of FIG. 9. Graph 240 in FIG. 24 illustrates the test results for the konus type expression member 164 of FIG. 10, and in FIG. 25, graph 250 shows the test results for the hard expression member 166 in FIG. 11. From these results, it should be recognized that body fluid was able to be successfully collected when the micro-sampler 100 was withdrawn within 75 ms of initial penetration, before reflexive action could occur, when an expression or pressurization force of 8.0N was applied to the skin with generally any of the expression units 90 tested. At the 6.0N force level, commercially acceptable sample collection success rates were achieved at the 75 ms time for the konus 164 and hard 166 expression units.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected.

The invention claimed is:

1. A method of sampling body fluid before reflexive action occurs, comprising:
   pressing an expression unit against skin;
   piercing the skin with a skin-piercing member that includes a fluid collection structure;
   collecting the body fluid with the fluid collection structure after said piercing the skin;

removing the skin-piercing member from the skin; and
said collecting the body fluid and said removing the skin-piercing member occur before the reflexive action occurs as a result of said piercing the skin, in which said collecting the body fluid and said removing the skin-piercing member occur within 150 ms from the beginning of said piercing the skin.

2. The method of claim 1, in which said collecting the body fluid includes collecting the body fluid with the skin-piercing member that has a tip with an open section that has a length of at least 350 μm and at most 600 μm.

3. The method of claim 2, in which the length of the open section is about 425 μm.

4. The method of claim 2, further comprising:
wherein the skin-piercing member includes a micro-sampler and the fluid collection structure includes an open capillary channel of the micro-sampler;
wherein the open section that has a length of about 425 μm;
wherein said pressing includes applying at least 10 N of force to the skin;
wherein said collecting the body fluid and said removing the skin-piercing member occur within 75 ms from the beginning of said piercing the skin;
wherein said collecting the body fluid includes collecting 20 nl to 1 μl of the body fluid; and
depositing the body fluid onto an analysis means of the micro-sampler within 200 ms of said piercing the skin.

5. The method of claim 1, wherein said collecting results in at least a 90% success rate.

6. The method of claim 1, in which said collecting the body fluid and said removing the skin-piercing member occur within 100 ms from the beginning of said piercing the skin.

7. The method of claim 1, in which said collecting the body fluid and said removing the skin-piercing member occur within 75 ms from the beginning of said piercing the skin.

8. The method of claim 1, further comprising:
detecting a predetermined force is reached with a pressure sensitive trigger; and
initiating said piercing the skin in response to said detecting.

9. The method of claim 1, in which said pressing includes applying at least 6 N of force to the skin.

10. The method of claim 1, in which said pressing includes applying at least 8 N of force to the skin.

11. The method of claim 1, in which said pressing includes applying at least 10 N of force to the skin.

12. The method of claim 1, in which said pressing includes applying at least 12 N of force to the skin.

13. The method of claim 1, in which said collecting the body fluid includes collecting 20 nl to 1 μl of the body fluid.

14. The method of claim 1, in which said collecting the body fluid includes collecting 200 to 300 nl of the body fluid.

15. The method of claim 1, wherein:
said piercing includes an extension phase where the piercing member extends to a maximum penetration depth followed by a withdraw phase where the piercing member retracts from the maximum penetration depth; and
the withdraw phase is longer than the extension phase.

16. The method of claim 15, in which said piercing includes maintaining the piercing member at a dwell depth beneath the skin during the withdraw phase.

17. The method of claim 1, further comprising:
wherein the fluid collection structure includes an open capillary channel; and
depositing the body fluid onto an analysis means within 200 ms of said piercing the skin.

18. The method of claim 17, in which said depositing occurs within 75 ms of said piercing the skin.

19. The method of claim 17, further comprising analyzing the body fluid with the analysis means.

20. The method of claim 1, further comprising:
said collecting the body fluid includes adhering body fluid on the outside of the skin-piercing member; and
drawing the body fluid on the outside of the skin-piercing member into the fluid collection structure after said removing the skin-piercing member from the skin.

21. The method of claim 1, further comprising:
analyzing the fluid sample within 10 seconds of said piercing.

22. The method of claim 1, further comprising:
said collecting the body fluid and said removing the skin-piercing member occur from 75 to 200 ms from the beginning of said piercing the skin.

23. A method of collecting fluid from skin to achieve a high collection success rate, comprising:
pressurizing the fluid beneath the skin by pressing an expression member against the skin;
penetrating the skin with a micro-sampler, wherein the micro-sampler has a shaft with a tip, an open capillary channel defined along the shaft, and an entrance of the capillary channel that is recessed 350 to 600 μm from the tip of the shaft;
withdrawing the micro-sampler from the skin at a speed slower than during said penetrating the skin; and
removing the micro-sampler completely from the skin with a sufficient fluid sample for accurate testing at least clung to the micro-sampler within 150 ms of said penetrating.

24. The method of claim 23, further comprising:
wherein said pressurizing includes pressing the expression member against the skin with at least 10 N of force;
wherein said removing occurs within 75 ms of said penetrating; and
wherein the entrance of the capillary channel is recessed about 425 μm from the tip of the shaft.

25. The method of claim 23, in which said pressurizing includes pressing the expression member against the skin with at least 6 N of force.

26. The method of claim 23, in which said removing occurs within 75 ms of said penetrating.

27. The method of claim 26, in which said pressurizing includes pressing the expression member against the skin with at least 8 N of force.

28. The method of claim 27, in which the expression member is ring-shaped.

29. The method of claim 28, in which the expression member includes a flexible cone-type expression ring.

30. The method of claim 27, in which the entrance of the capillary channel is recessed about 425 μm from the tip of the shaft.

31. The method of claim 23, in which said pressurizing includes pressing the expression member against the skin with at least 8 N of force.

32. The method of claim 23, in which said pressurizing includes pressing the expression member against the skin with at most 12 N of force.

33. The method of claim 23, in which the sufficient fluid sample for accurate testing is at least 200 nl and at most 1 μl.

34. The method of claim 23, further comprising:
drawing at least some of the fluid clung to the micro-sampler that is outside the capillary channel into the capillary channel after said removing the micro-sampler completely from the skin.

35. The method of claim 23, further comprising:
drawing the sufficient fluid sample for accurate testing is inside the capillary channel before said removing the micro-sampler completely from the skin.

36. The method of claim 23, further comprising:
firing the micro-sampler when the expression member is pressed at least to a predetermined force against the skin.

37. The method of claim 23, further comprising depositing the fluid sample onto an analysis means of the micro-sampler before significant evaporation of the fluid sample occurs.

38. The method of claim 37, in which said depositing the fluid sample onto the analysis means occurs within about 500 ms of said penetrating the skin.

39. The method of claim 38, in which said depositing the fluid sample onto the analysis means occurs within about 75 ms of said penetrating the skin.

40. The method of claim 23, further comprising:
loading the micro-sampler into a meter before said penetrating the skin; and
unloading the micro-sampler from the meter after said removing the micro-sampler completely from the skin.

41. An apparatus, comprising:
a micro-sampler configured to collect body fluid from skin, the micro-sampler including
a body,
a shaft with a pointed tip extending from the body to penetrate the skin,
an open capillary channel extending along the shaft with a capillary channel opening for collecting the body fluid via capillary action, the capillary channel being hydrophilic, the capillary channel opening being located between 350 to 600 μm from the pointed tip; and
wherein the shaft has an open section located between the capillary channel opening and the pointed tip, the open section being configured to provide an insufficient contact area to draw fluid via capillary action.

42. The apparatus of claim 41, wherein the capillary channel opening is located about 425 μm from the pointed tip.

43. The apparatus of claim 41, the pointed tip having a blade angle from 20° to 40°.

44. The apparatus of claim 41, the capillary channel having an aspect ratio from 0.7 to 1.6.

45. The apparatus of claim 41, further comprising:
a firing mechanism for firing the micro-sampler into the skin, the firing mechanism including a pressure sensitive trigger configured to fire the firing mechanism when at least 6 N of force is applied against the skin.

46. The apparatus of claim 41, further comprising:
a meter in which the micro-sampler is loaded, the meter including an expression ring made from a hard inner ring that is over molded with a flexible material.

47. The apparatus of claim 41, further comprising:
the capillary channel opening being located about 425 μm from the pointed tip;
the pointed tip having a blade angle from 20° to 40°; and
the capillary channel having an aspect ratio from 0.7 to 1.6.

* * * * *